US012280142B2

(12) United States Patent
Meyer et al.

(10) Patent No.: US 12,280,142 B2
(45) Date of Patent: Apr. 22, 2025

(54) COMPOSITIONS FOR PREVENTING INFECTION

(71) Applicant: Altamira Medica AG, Zug (CH)

(72) Inventors: Thomas Meyer, Zuchwil (CH); Fabio Fais, Kembs (FR)

(73) Assignee: Altamira Medica AG, Zug (CH)

(*) Notice: Subject to any disclaimer, the term of this patent is extended or adjusted under 35 U.S.C. 154(b) by 0 days.

(21) Appl. No.: 17/466,142

(22) Filed: Sep. 3, 2021

(65) Prior Publication Data

US 2022/0071893 A1  Mar. 10, 2022

Related U.S. Application Data

(60) Provisional application No. 63/230,191, filed on Aug. 6, 2021, provisional application No. 63/173,816, filed on Apr. 12, 2021, provisional application No. 63/119,237, filed on Nov. 30, 2020, provisional application No. 63/075,590, filed on Sep. 8, 2020.

(51) Int. Cl.
| | | |
|---|---|---|
| *A61K 9/00* | (2006.01) | |
| *A61K 33/00* | (2006.01) | |
| *A61K 47/10* | (2017.01) | |
| *A61K 47/12* | (2006.01) | |
| *A61K 47/14* | (2017.01) | |
| *A61K 47/36* | (2006.01) | |
| *A61P 31/16* | (2006.01) | |

(52) U.S. Cl.
CPC .............. *A61K 9/006* (2013.01); *A61K 33/00* (2013.01); *A61K 47/10* (2013.01); *A61K 47/12* (2013.01); *A61K 47/14* (2013.01); *A61K 47/36* (2013.01); *A61P 31/16* (2018.01)

(58) Field of Classification Search
None
See application file for complete search history.

(56) References Cited

U.S. PATENT DOCUMENTS

| | | |
|---|---|---|
| 6,110,479 A | 8/2000 | Blaney et al. |
| 6,638,521 B2 | 10/2003 | Dobrozsi |
| 8,535,646 B2 | 9/2013 | Sokol et al. |
| 8,894,604 B2 | 11/2014 | Vecellio-None et al. |
| 8,992,893 B2 | 3/2015 | Sokol et al. |
| 10,342,820 B2 | 7/2019 | Grassauer et al. |
| 10,398,465 B2 | 9/2019 | Sokol et al. |
| 10,426,761 B2 | 10/2019 | Ghannoum et al. |
| 2003/0219472 A1* | 11/2003 | Pauletti ................. A61K 45/06 514/3.3 |
| 2006/0045868 A1 | 3/2006 | Meezan et al. |
| 2006/0045869 A1 | 3/2006 | Meezan et al. |
| 2007/0031512 A1 | 2/2007 | Hughes |
| 2007/0224293 A1 | 9/2007 | Hughes et al. |
| 2008/0299079 A1 | 12/2008 | Meezan et al. |
| 2015/0031729 A1 | 1/2015 | Ghannoum et al. |
| 2017/0189539 A1* | 7/2017 | Burstedt ................. A61K 47/26 |
| 2018/0228857 A1* | 8/2018 | Toh ......................... A61P 37/08 |

FOREIGN PATENT DOCUMENTS

| | | |
|---|---|---|
| EP | 0 733 357 A1 | 9/1996 |
| EP | 1 343 472 B1 | 9/2003 |
| EP | 1 374 856 A1 | 1/2004 |
| EP | 2 101 792 B1 | 9/2009 |
| EP | 2 178 533 B1 | 4/2010 |
| KR | 10-1474858 B1 | 12/2014 |
| WO | WO 91/06283 A1 | 5/1991 |
| WO | WO 00/47184 A1 | 8/2000 |
| WO | WO 01/51014 A1 | 7/2001 |
| WO | WO 02/051379 A2 | 7/2002 |
| WO | WO 2008/067982 A2 | 6/2008 |
| WO | WO 2009/027057 A1 | 3/2009 |
| WO | WO 2011/029218 A1 | 3/2011 |
| WO | WO 2012/067932 A1 | 5/2012 |
| WO | WO 2017/023162 A1 | 2/2017 |
| WO | WO-2022053412 A1 | 3/2022 |

OTHER PUBLICATIONS

Choudhury, H., et al., Journal of Pharmaceutical Sciences 106: 1736 â 1751 (2017). (Year: 2017).*
Abduljauwad et al., "Nano-clays as Potential Pseudo-antibodies for COVID-19," Nanoscale Research Letters, Nanoscale Research Letters, vol. 15, No. 1, Aug. 28, 2020, 12 pages.
International Search Report and Written Opinion mailed on Nov. 19, 2002, for International Application No. PCT/EP01/14655, 6 pages.
International Search Report and Written Opinion mailed on Jan. 4, 2022, for International Application No. PCT/EP2021/074417, 16 pages.
Written Opinion mailed on Jun. 17, 2010, for International Application No. PCT/CN2009/001187, 6 pages.
Ando et al., "Nasal Insulin Delivery in Rabbits Using Soybean-Derived Sterylglucoside and Sterol Mixtures as Novel Enhancers in Suspension Dosage Forms," *Biol. Pharm. Bull.* 21(8):862-865, 1998.
Balakrishnan et al., "Carbopol-Incorporated Thermoreversible Gel for Intranasal Drug Delivery," *Molecules* 20:4124-4135, 2015.
Bishai et al., "Stability of different viruses in a newly developed transport medium," *Can. J. Microbiol.*, 20:75-80, 1974.
Cho et al., "Poloxamer/Cyclodextrin/Chitosan-Based Thermoreversible Gel for Intranasal Delivery of Fexofenadine Hydrochloride," *Journal of Pharmaceutical Sciences* 100(2):681-691, 2011.
Choi et al., "Intranasal distribution and clearance of thermoreversible gel in an animal model," *International Forum of Allergy & Rhinology* 7(7):705-711, 2017.
Chonkar et al., "Smart Polymers in Nasal Drug Delivery," *Indian J Pharm Sci* 77(4):367-375, 2015.
Dell, D. J., "Smectite Clays In Personal Care Products," *Cosmetics & Toiletries* 108:79-85, 1993.
Diethart et al., "Hydroxypropylmethylcellulose gel application delays Der p 1 diffusion in vitro," *Natural Science* 2(2):79-84, 2010.
Djupesland, "Nasal drug delivery devices: characteristics and performance in a clinical perspective—a review," *Drug Deliv. and Transl. Res.* 3:42-62, 2013.
Emberlin et al., "A double blind, placebo-controlled trial of inert cellulose powder for the relief of symptoms of hay fever in adults," *Current Medical Research and Opinion* 22(2):275-285, 2006.
Heimdahl, "Prevention and management of oral infections in cancer patients," *Support Care Cancer* 7:224-228, 1999.

(Continued)

Primary Examiner — David J Blanchard
Assistant Examiner — Daniel F Coughlin
(74) Attorney, Agent, or Firm — COOLEY LLP

(57) ABSTRACT

The present disclosure relates aqueous composition comprising a mucoadhesive polymer and clay particles and methods of treating or preventing infection.

24 Claims, 4 Drawing Sheets

(56) References Cited

OTHER PUBLICATIONS

Khutoryanskiy, "Advances in Mucoadhesion and Mucoadhesive Polymers," *Macromol. Biosci. 11*:748-764, 2011.

Kirk-Othmer et al., Encyclopedia of Chemical Technology, Fourth Edition, 6:381-423, Chlorocarbons and Chlorohydrocarbons-C2 to Combustion Technology, John Wiley & Sons, Inc. 1993.

Sharma et al., "Formulation and characterization of intranasal mucoadhesive nanoparticulates and thermo-reversible gel of levodopa for brain delivery," *Drug Dev Ind Pharm 40*(7):869-878, 2014.

Anonymous: "Vanatural XGB—Bentonite and Xanthan Gum Blend", Vanderbilt Minerals, LLC, Jan. 12, 2024, pp. 1-1, XP055873560, Retrieved from the Internet: URL:https://www.vanderbiltminerals.com/resources/VANATURAL_XGB_TDS.pdf [retrieved on Mar. 26, 2024] the whole document.

Fink "Gastrointestinal mucosal injury in experimental models of shock, trauma, and sepsis". Critical care medicine. May 1, 1991; 19(5): 627-41.

Khan et al., "Infection and mucosal injury in cancer treatment". JNCI Monographs. Oct. 1, 2001; 2001(29): 31-6.

Yang et al., "Concentrations and size distributions of airborne influenza A viruses measured indoors at a health centre, a day-care centre and on aeroplanes". Journal of the Royal Society Interface. Aug. 7, 2011; 8(61): 1176-84.

\* cited by examiner

FIG. 1

Reduction of viral charge after bentonite incubation

[Bar chart showing Log reduction vs Bentonite & SARS-CoV-2 incubation time (5 min, 15 min, 45 min) with four conditions: Veegum Bentonite 0.04%, Veegum Bentonite 0.08%, Veegum Bentonite 0.16%, Vicks First defence (diluted 10x)]

| Log | Viral reduction |
|-----|-----------------|
| 1   | 90%             |
| 1.8 | 98.42%          |
| 2   | 99%             |
| 3   | 99.90%          |
| 4   | 99.99%          |

COMPOSITIONS FOR PREVENTING INFECTION

CROSS-REFERENCE TO RELATED APPLICATIONS

This application claims the benefit of priority to U.S. Application Ser. No. 63/230,191, filed Aug. 6, 2021, U.S. Application Ser. No. 63/173,816, filed Apr. 12, 2021, U.S. Application Ser. No. 63/119,237, filed Nov. 30, 2020, and U.S. Application Ser. No. 63/075,590, filed Sep. 8, 2020, the contents of each of which are hereby incorporated by reference in their entireties for all purposes.

BACKGROUND

Respiratory viral infections such as influenza and coronavirus are significant causes of respiratory disease worldwide. Influenza causes more than 250,000 deaths annually in the industrialized world. The 1918 pandemic, estimated to have killed at least twenty million people worldwide, was caused by a particular influenza viral strain and was characterized by both rapid transmission and severe symptoms.

Even without a pandemic, influenza infection presents both a health risk and health cost. On average, 5% to 20% of the U.S. population contracts influenza (commonly called "the flu") each year. More than 100,000 people are hospitalized from flu complications, and approximately 36,000 people die. Some people, such as older people, young children, and people with certain health conditions (e.g. immunocompromised people), are at high risk for serious flu complications.

Influenza A and B viruses are responsible for seasonal flu epidemics each year. Over the course of a flu season, different types (A & B) and subtypes of influenza A viruses can circulate through the population and cause illness. A particular problem for treatment strategies is the fact that influenza viruses are constantly changing through a process called "antigenic drift." Thus, a vaccine that might have been useful last year may be less effective or ineffective this year.

Most recently, the 2019-2020 coronavirus 2019 (COVID-19) pandemic is caused by severe acute respiratory syndrome coronavirus 2 (SARS-CoV-2). The outbreak was first identified in Wuhan, Hubei, China, in December 2019, and was recognized as a pandemic by the World Health Organization (WHO) on Mar. 11, 2020. As of November 2020, there have been over 62 million cases of COVID-19 reported globally, resulting in over 1.4 million deaths.

There has been a longstanding need for devices, compositions, and other treatments that will effectively prevent or inhibit the transmission of communicable diseases. Attempts at solving this problem include wearing masks or respirators and avoiding or quarantining of individuals or animals that are known or expected to be sick or carrying germs. Such approaches are common in certain countries where masks are worn by persons encountering contaminated environments such as public transportation or public gathering places.

While numerous solutions exist for killing microorganisms once they have contacted a person or animal, the effectiveness of such solutions is dependent on quick recognition of the microorganism contact and application of the microbicidal composition prior to the microorganism binding to a mucosa, whereby it would enter the body and infect the individual. For example, washing with an anti-bacterial soap may be effective for killing germs on the hands; however, it is very easy for a person to unwittingly touch a contaminated surface and put their hands near or in their mouth or nose before washing their hands.

Similarly, allergic responses to inhaled allergens are quite common and afflict a significant portion of the population—ranging from 10-30% of children and adults worldwide. While allergic symptoms can be mild, even relatively mild conditions such allergic rhinitis can develop complications such as the development of nasal polyps, sinusitis, middle ear infections, etc. Further, therapies for treating allergies (antihistamines, decongestants, and oral corticosteroids) can have significant side effects (e.g., cardiovascular effects, weight gain, insomnia, irritability, hypertension, immune suppression, etc.) and thus may not be desirable as long-term therapies.

Physical devices such as masks are uncomfortable, and often ineffective for avoiding contact with microorganisms and allergens. Solutions for killing microorganisms that have already contacted the body are often ineffective for prevention of infection since they are intermittent, transitory options that do not provide sustained protection. There is an unmet need for a composition that is capable of forming a barrier against airborne pathogens including microorganisms and allergens. This invention meets this, among other needs.

SUMMARY OF THE DISCLOSURE

In some embodiments, the present disclosure provides an aqueous composition comprising a mucoadhesive polymer and clay particles. The mucoadhesive polymer may be one or more of sodium alginate, chitosan, guar gum, xanthan gum, pectin, hydroxyethyl cellulose, hydroxypropyl cellulose, hydroxypropylmethyl cellulose, sodium carboxymethyl cellulose, poly(ethylene oxide), poly(acrylic acid), poloxamer (e.g. poloxamer 407), Avicel (e.g. Avicel RC591), and combinations thereof. In some embodiments, the mucoadhesive polymer is xanthan gum. The clay particles may be one or more of kaolin minerals such as kaolinite, china clay, dickite, nacrite, halloysite; serpentine minerals such as lizardite, halloysite, chrysotile, antigorite, carlosturanite, amestite, cronstedite, chamosite, berthierine, garierite; talc; pyrophyllite; ferripyrophyllite; smectites such as montmorillonites, beidellite, nontronite, hectorite, saponite, sauconite, medmontite, pimelite, bentonite; illite minerals such as ledikete, bravaisite, degraded mica, hydromica, hydromuscovite, hydrous illite, hydrous mica, K-mica, micaceous clay, and sericite; mica such as pegmatite, muscovite, and phlogopite; brittle mica such as margarite, and clintonite; glauconite; celadonite; chlorite and vermiculite such as pennine, clinochlore, chamosite, nimite, baileychlore, donbassite, cookite, sudoite, franklinfurnaceite; palygorskite and sepiolite minerals such as attapulgite; allophane and imogolite; mixed layer clay minerals such as talc-chlorite. In some embodiments, the clay particles are bentonite particles.

In some embodiments, the composition comprises about 0.1% to about 3% by weight of the mucoadhesive polymer and about 0.4% to about 5% by weight of clay. For example, the composition comprises about 0.1% to about 3% by weight of xanthan gum and about 0.4% to about 5% by weight of bentonite clay. The pH of the composition may be from about 4 to about 8, for example from about 5 to about 7. In some embodiments, the composition further comprises a buffer and/or a flavorant. In some embodiments, the composition includes one or more lipophilic excipients (e.g. caprylic/capric triglyceride). In some embodiments, the composition comprises about 0.1% to about 50% by weight of the lipophilic excipients. In some embodiments, the composition does not include a lipophilic excipient. In some embodiments, the composition includes one or more moisturizing agents (e.g. glycerol). In some embodiments, the moisturizing agents comprise about 0.1% to about 5% by weight of the composition. In some embodiments, the composition includes one or more viscosity modifiers (e.g. glyceryl stearate). In some embodiments, the composition comprises about 0.1% to about 50% by weight of the viscosity modifiers. In some embodiments, the composition includes one or more preservatives and/or chelating agents (e.g. potassium sorbate, methyl paraben, and/or disodium EDTA). In some embodiments, the composition comprises about 0.01% to about 3% by weight of the preservatives and/or chelating agents.

In some embodiments, the composition comprises one or more preservatives. In some embodiments, the composition has no more than 0.5% by weigh of preservative. In some embodiments, the composition. is free of preservatives. In some embodiments, the composition is thixotropic. In some embodiments, the composition exhibits non-Newtonian shear thinning viscosity. In some embodiments, the composition is an aqueous solution or a gel emulsion (oil in water gel).

In some embodiments, the present disclosure provides methods of treating or preventing infection in a subject comprising administering a therapeutically effective amount of the aqueous composition of the present disclosure to the subject's mucosa, wherein the composition forms a barrier on the mucosa. In some embodiments, the mucosa is a nasal, oral or pharyngeal mucosa. In some embodiments, the infection is a respiratory viral infection. In some embodiments, the respiratory viral infection is one or more of influenza, rhinovirus, coronavirus, respiratory syncytial virus, and/or paramyxovirus infection. For example, the infection may be a coronavirus infection selected from Severe Acute Respiratory Syndrome-Corona Virus (SARS-CoV), Middle East Respiratory Syndrome virus (CoV-MERS), human HCoV-229E, HCoV-OC43, HCoV-NL63 and HCoV-HKU1. In some embodiments, the coronavirus infection is SARS-CoV-2. In some embodiments, the composition is administered as a spray or aerosol, for example via a nasal pump. In some embodiments, the composition comprises about 0.1% to about 3% by weight of xanthan gum and about 0.4% to about 5% by weight of bentonite clay.

In some embodiments, the present disclosure provides methods of preventing a COVID-19 infection in a subject, comprising administering a therapeutically effective amount of the aqueous composition of the present disclosure, wherein the composition forms a barrier on the mucosa. In some embodiments, the composition traps and/or binds to a virus, such as the SARS-CoV-2 virus. In some embodiments, the composition comprises about 0.1% to about 3% by weight of xanthan gum and about 0.4% to about 5% by weight of bentonite clay.

BRIEF DESCRIPTION OF THE DRAWINGS

FIG. 1 shows the reduction of viral charge after incubation with bentonite for 5, 15, and 45 minutes. For each time point results are shown from left to right for bentonite 0.04%, bentonite 0.08%, bentonite 0.16% and Vicks First Defence, a nasal spray comprising hydroxypropyl methylcellulose (diluted 10-fold). A 1-log reduction corresponds to a 90% reduction in viral load, a 1.8-log reduction corresponds to a 98.42% reduction, a 2-log reduction corresponds to a 99% reduction, and a 3-log reduction corresponds to a 99.9% reduction.

DETAILED DESCRIPTION

Figure 2:
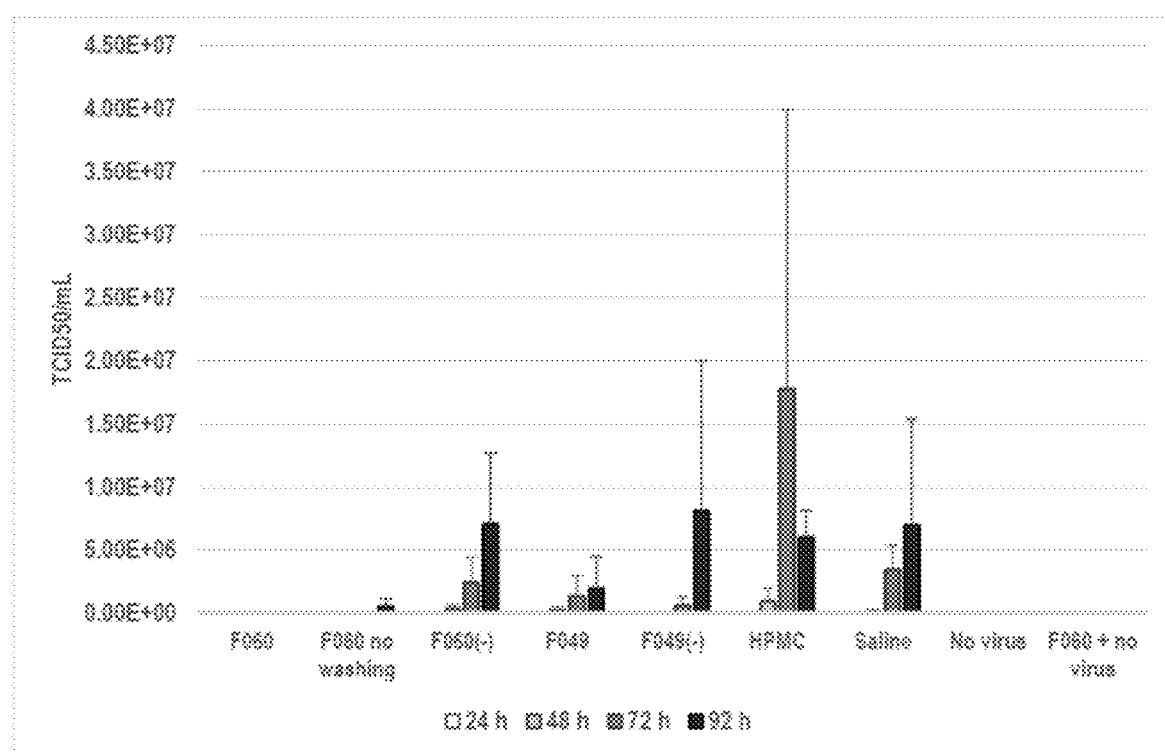
FIG. 2 shows mean SARS-CoV-2 viral titer (with standard deviation) quantified after infection of reconstituted human nasal epithelial cells at 24, 48, 72 and 96 h post infection under different treatments (n=3 each). Cell cultures were treated every day with bentonite formulation F060, the same formulation, but without daily washing of the apical side, with vehicle F060(−), bentonite formulation F049, its vehicle F049(−), HPMC 5 mg/mL, or saline (main control). Non-infected untreated cells and non-infected cells treated with formulation F060 served as further control groups. In the positive control group, clear virus growth could be observed 48 h after infection and virus titers increased over 96 h to a mean of 6.9×106 TCID50/mL. In comparison, in nasal epithelium treated with the bentonite composition F060, mean virus titers with apical washing were 90.0% lower at 48 h (p<0.05) and 99.2 and 99.4% lower at 72 and 96 h, respectively (p<0.001). Without apical washing, mean virus titers were 92.4% lower at 96 h (p<0.001). Treatment with bentonite composition F049 resulted in reduced viral titers as well, however, the reduction became apparent later and was smaller than with F060 (61.1% at 72 h and 71.8% at 96 h; not significant). The vehicles F060(−) and F049(−) appeared to have no effect on viral growth and viral titers. Treatment with HPMC showed no significant effect, either. The culture control as well as the non-infected culture treated with F060 appeared inconspicuous.

The present disclosure is based on the surprising discovery that by combining certain mucoadhesive polymers and clay in an aqueous composition in specific amounts, the composition has rheological properties that provide relatively low viscosity when applying the composition (e.g., by spraying or flushing the nasal or oropharyngeal cavity with the composition), yet has a relatively high viscosity that resists ciliary clearance or dislodgement for a sufficient time to provide a therapeutic and/or barrier effect to protect the user from pathogens or allergens. Such rheological properties include, for example, fluid compositions that are "shear thinning" or thixotropic such that when a shear force can be applied to the composition, the viscosity becomes low enough to be readily delivered to the nose or mouth of the patient via conventional delivery devices known in the art (e.g. spray pump or spray bottle, "RetroNose" device as described in U.S. Pat. No. 8,894,604, herein incorporated by reference, breath-actuated pressurized metered dose inhaler (pMDI), etc.), yet the composition quickly reverts to a higher viscosity after deposition on a surface, such as the mucosal surface, whereupon the viscous properties bind it to the mucosal surface and the gel forms a protective barrier against pathogens while simultaneously inactivating pathogens. Without being bound to a particular mechanism, the trapping or binding of pathogens can occur via physical interactions with the clay component of the composition, such as ionic interactions.

The mucosal lining of the nose, mouth, gut, and body cavities of mammals represents the first barrier to the entry of pathogenic microorganisms or allergens to mammalian bodies where they can cause both local and systemic infections or allergic reactions. The epithelial mucosal lining forms a barrier that reduces the entry of commensals organisms (Monica Boirivanta and Warren Strober, "The Mechanism of Action of Probiotics" Current Opinion in Gastroenterology 2007, 23:679-692).

In this application, methods and compositions are disclosed that block, trap or neutralize microorganisms that cause infectious disease from contacting or infecting the mucosa, which in turn prevents microorganisms from disseminating into body and causing infection. Similarly, methods and compositions are disclosed that block or neutralize allergens that are inhaled or otherwise contact the mucosal tissues of a patient. The methods and compositions of the present disclosure, in various embodiments, incorporate a mucoadhesive polymer and clay particles that can block, trap or neutralize microorganisms (bacteria, fungi, and viruses) known to cause infections, or adsorb, bind or block allergens from contacting the patients oral or nasal mucosa. The method protects human mucosa by forming a barrier layer, and includes clay (e.g., bentonite) particles that can bind or inhibit microorganisms (bacteria, fungi and viruses), or adsorb or bind to allergens. This dual action composition and method (barrier plus clay) can be applied to human or other mammalian mucosal tissues or, for example, surfaces in the oral cavity, nasal cavity, vaginal cavity, throat, and other orifices, including, but not limited to, the ears. It can also be applied to medical devices, such as tracheal devices, catheters (e.g. irrigation catheters), syringes, and the like. This unique and unexpected solution addresses a long-felt but unresolved need for preventing communicable diseases caused by airborne microorganisms. Further, because the composition utilizes a natural mineral rather than an antimicrobial agent, there is no risk of pathogenic resistance.

A barrier-forming composition that is safe (i.e. does not cause damage to the mucosa) and forms a barrier that inhibits the passage of pathogenic microbes (e.g., influenza viri, COVID-SARS2), or allergens to or through the mucosal tissues is desirable. Another desirable property is an ability to inhibit microbial growth through immobilizing or binding pathogens, or in some embodiments, microbicidal activity, for an extended period of time. Without being bound by theory, the mechanism of action of the barrier-forming composition disclosed herein is, in some embodiments, based on a synergistic dual-action mechanism, in which germs are trapped in the formed barrier, and subsequently bound or inactivated by the clay.

The methods and compositions described herein may be particularly useful when a human, or more generally, a mammal, has a disrupted mucosa. A disruption may be caused by a wound or scratch. The mucosa of the oral cavity and gastrointestinal (GI) tract serve as an important mechanical barrier that helps to prevent a local or systemic invasion of various microbes and the absorption of microbial products that are normally present in the oral cavity and the lumen of the gut. "Gastrointestinal mucosal injury in experimental models of shock, trauma, and sepsis," Crit. Care Med. 1991; 19:627-41). Derangement in the barrier function of the mucosa plays a central role in the pathophysiology of systemic infection. In other words, disruption of this mucosa will lead to infections.

Elimination or reduction of the risk of a breach in the first line of defense is important, and the maintenance of mucosal integrity is important. (Anders Heimdahl, "Prevention and Management of Oral Infections in Cancer Patients" Supportive Care in Cancer, Vol. 7, No. 4, 224-228 (1999).) Thus, having an intact mucosa is an important host defense against systemic infection, particularly in immunocompromised patients (e.g. cancer patients). (Shahab A. Khan, John R. Wingard, "Infection and Mucosal Injury," Cancer Treatment Journal of the National Cancer Institute, Monographs No. 29 (2001). A barrier-forming composition that blocks and binds harmful microorganisms and that does not interfere with healing of a disrupted mucosa is a unique and unexpected solution to the susceptibility of the problems of those with disrupted mucosa, particularly those that also have immunodeficiency.

Definitions

While the following terms are believed to be well understood by one of ordinary skill in the art, the following definitions are set forth to facilitate explanation of the presently disclosed subject matter.

Throughout the present specification, the terms "about" and/or "approximately" may be used in conjunction with numerical values and/or ranges. The term "about" is understood to mean those values near to a recited value. For example, "about 40 [units]" may mean within +25% of 40 (e.g., from 30 to 50), within ±20%, +15%, +10%, +9%, ±8%, ±7%, ±6%, ±5%, +4%, ±3%, ±2%, +1%, less than +1%, or any other value or range of values therein or therebelow. In other contexts, the term "about" may refer to a value intermediate between adjacent values in a numerical sequence. Furthermore, the phrases "less than about [a value]" or "greater than about [a value]" should be understood in view of the definition of the term "about" provided herein. The terms "about" and "approximately" may be used interchangeably.

Throughout the present specification, numerical ranges are provided for certain quantities. It is to be understood that these ranges comprise all subranges therein. Thus, the range "from 50 to 80" includes all possible ranges therein (e.g., 51-79, 52-78, 53-77, 54-76, 55-75, 60-70, etc.). Furthermore, all values within a given range may be an endpoint for the range encompassed thereby (e.g., the range 50-80 includes the ranges with endpoints such as 55-80, 50-75, etc.).

The term "a" or "an" refers to one or more of that entity; for example, "a mucoadhesive polymer" refers to one or more mucoadhesive polymers or at least one mucoadhesive polymer. As such, the terms "a" (or "an"), "one or more" and "at least one" are used interchangeably herein. In addition, reference to "an excipient" by the indefinite article "a" or "an" does not exclude the possibility that more than one excipient is present, unless the context clearly requires that there is one and only one of the excipients.

As used herein, the verb "comprise" as is used in this description and in the claims and its conjugations are used in its non-limiting sense to mean that items following the word are included, but items not specifically mentioned are not excluded. The present invention may suitably "comprise", "consist of", or "consist essentially of", the steps, elements, and/or reagents described in the claims.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

The term "treat," "treated," "treating" or "treatment" includes the diminishment or alleviation of at least one symptom associated or caused by the state, disorder or disease being treated. Treatment can be diminishment of one or several symptoms of a disorder or complete eradication of a disorder or a disease. Similarly, the term "prophylaxis" refers to the partial or total prevention of symptoms by administration of the active agent prior to the expected initiation of such symptoms.

As used herein, the term "subject," "individual" or "patient" is used interchangeably and refers to a vertebrate, preferably a mammal. Non-limiting examples include mice, dogs, rabbits, farm animals, sport animals, pets, and humans.

As used herein, "therapeutically effective amount" or an "effective amount" indicates an amount that results in a desired pharmacological and/or physiological effect for the condition. The effect may be prophylactic in terms of completely or partially preventing a condition or symptom thereof and/or may be therapeutic in terms of a partial or complete cure for the condition and/or adverse effect attributable to the condition.

The term "mucoadhesive composition" refers to a composition that adheres to the mucosa or mucosal surface. The mucoadhesion can occur by any mechanism, including, but not limited to, electrostatic attraction, hydrogen bonding, low surface tension, and polymer diffusion into the mucosal layer. The term "mucosa" or "mucosal surface" refers to any surface or anatomical location over which mucus is produced. "Mucosa" and "mucosal surface" include, but are not limited to, the oral, nasal, ocular, aural, vaginal, anal, gastric, and intestinal cavities.

The term "mucoadhesive polymer" refers to compounds that adhere to the mucosa or mucosal surface. Mucoadhesive polymers include all classes of mucoadhesive polymers, including anionic polymers (e.g., alginate, xanthan gum, carrageenan, poly(acrylic acid), poly-(methacrylic acid), poly[(maleic acid)-co-(vinyl methyl ether)]), cationic polymers (e.g., chitosan), substituted cellulosic polymers such as Avicel RC591 (mixture of carboxymethyl cellulose and microcrystalline cellulose, hydroxyethyl cellulose), non-ionic polymers (e.g., guar gum, galactomannan, glucomannan, amphoteric polymers, polymeric thiomers, polymers with acrylate end groups, dendrimers, boronic acid copolymers, synthetic glycopolymers, poloxamers such as poloxamer 407 (Lutrol F127), gums such as xanthan gum, pectin, and polymeric blends and complexes), amphoteric polymers, acrylate-terminated polymers, dendrimers, boronic acid copolymers, synthetic glycopolymers, and any polymers described in Khutoryanskiy, *Macromolecular Bioscience*, 11(6) 748-64 (2011), which is hereby incorporated by reference in its entirety.

Methods

In some embodiments, a barrier-forming composition may be administered to prevent or treat an infectious disease in a mammal. Prevention means that the risk of infection from microorganisms encountered, or an allergic reaction to allergens encountered subsequent to application of the barrier-forming composition is reduced. For the full preventive effect, the barrier-forming composition should be applied prior to the mammal encountering a contaminated environment or item. Some benefit (e.g., reduction in severity of symptoms) can also be obtained from administering the barrier-forming composition during or after the encounter with a contaminated environment or item. For example, application of a composition of the present disclosure can reduce the "shedding" of pathogens (e.g., influenza viruses, COVID-SARS2 viruses, etc.) after infection, and thus reduce the severity of symptoms In some embodiments, a barrier-forming composition is administered to a mammal with a disrupted mucosa, such as for example an immunocompromised mammal. The disrupted area in a mucosa of the mammal is identified and a therapeutically effective amount of a barrier-forming composition is administered to at least the disrupted area of the mucosa of the mammal. The barrier-forming composition provides a barrier on the disrupted area of the mucosa that effectively inhibits microorganisms from disseminating to a disrupted area of the mucosa.

The barrier-forming composition is effective against microorganisms or allergens with a diameter of, for example, about 30 nm or greater, such as about 100 nm (HIV, spherical), about 100 to about 300 nm (influenza, spherical and elongated forms), about 120 nm to about 260 nm (EBV spherical/diskforms), and about 30 nm (rhinovirus, spherical). Thus, the composition should also be effective against other microorganisms with diameters of about 30 nm, or greater than about 30 nm.

Thus, the present invention provides methods of treating, ameliorating, preventing, or reducing infectious disease or the symptoms thereof caused by a pathogens or potential pathogens in mammals, preferably humans. Examples of pathogens include viruses, bacteria, parasites, and fungus. In certain aspects, the pathogen is a virus. The virus can be from the Adenoviridae, Coronaviridae, Filoviridae, Flaviviridae, Hepadnaviridae, Herpesviridae, Orthomyxoviridae, Paramyxovirinae, Pneumovirinae, Picornaviridae, Poxyiridae, Retroviridae, or Togaviridae family of viruses. In some embodiments the virus is the cause of an upper or lower respiratory infection. Representative medically relevant examples include, but are not limited to rhinovirus, coronavirus, parainfluenza virus, adenovirus, enterovirus, respiratory syncytial virus (RSV), bocavirus, influenza viruses, human metapneumovirus (hMPV), orthomyxoviridae, cytomegalovirus, Epstein-Barr virus, herpes simplex virus, and morbillivirus. In embodiments, the virus is the cause of an infection of the skin or mucosal tissues. Examples of mucous membranes include lips, mouth, nasal cavity and sinuses, middle ear, the eustachian tube, pharynx, the lining of the urogenital tract (including urethra and vagina), the lining of the respiratory tract, and the eyes (conjunctival membranes). Examples of viruses causing infections of the skin and mucosal tissues include herpes virus, including herpes simplex, varicella zoster, and herpes zoster virus, human papillomavirus, molluscum contagiosum virus, coxsackievirus, adenovirus, or pox virus.

In yet a further aspect, the pathogens or potential pathogens being treated or protected against are a bacteria. Representative bacilli include, but are not limited to *Hemophilus influenzae, Klebsiella pneumoniae, Legionella pneumophila, Pseudomonas aeruginosa, Escherichia coli, Proteus mirabilis, Enterobacter cloacae, Serratia marcescens, Helicobacter pylori, Salmonella enteritidis*, and *Salmonella typhi, Listeria, Staphylococcus, Streptococcus, Enterococcus*, Actinobacteria and *Clostridium*. In some embodiments the bacteria is the cause of an upper or lower respiratory infection.

In another embodiment, the pathogens or potential pathogens being treated or protected against are a NIAID Category A-C priority pathogens. Representative Category A Priority Pathogens include, but are not limited to *Bacillus anthracis* (anthrax), *Clostridium botulinum* toxin (botulism), *Yersinia pestis* (plague), Variola major (smallpox), *Franci-*

*sella tularensis* (tularemia), Arenaviruses, Bunyaviruses, Flaviruses, and Filoviruses. Representative Category B Priority Pathogens include, but are not limited to *Burkholderia pseudomallei* (melioidosis), *Coxiella burnetii* (Q fever), *Brucella* species (brucellosis), *Burkholderia mallei* (glanders), *Chlamydia psittaci* (Psittacosis), Typhus fever, Food- and waterborne pathogens (Diarrheagenic *E. coli*, Pathogenic Vibrios, *Shigella* species, *Salmonella, Listeria monocytogenes, Campylobacter jejuni, Yersinia enterocolitica*), Caliciviruses, Hepatitis A, *Cryptosporidium parvum, Cyclospora cayatanensis, Giardia lamblia, Entamoeba histolytica, Toxoplasma gondii, Naegleria fowleri, Balamuthia mandrillaris*, Microsporidia, Mosquito-borne encephalitis viruses (West Nile virus, LaCrosse encephalitis, California encephalitis, Venezuelan equine encephalitis, Eastern equine encephalitis, Western equine encephalitis, Japanese encephalitis virus, St. Louis encephalitis virus). Representative Category C Priority Pathogens include, but are not limited to, Nipah virus, Hendra virus, additional hantaviruses, Tickborne hemorrhagic fever viruses (Bunyaviruses and Flaviruses), Tickborne encephalitis complex flaviviruses (Tickborne encephalitis viruses, European subtype Far Eastern subtype, Siberian subtype, Powassan/Deer Tick virus), Yellow fever virus, Tuberculosis, including drug-resistant TB, influenza virus, Other Rickettsias, Rabies virus, Prions, Chikungunya virus, *Coccidioides* spp., Severe Acute Respiratory Syndrome Associated Coronavirus (SARS-CoV), MERS-CoV, and other highly pathogenic human coronaviruses.

In some embodiments, the methods of the present disclosure prevent or treat a respiratory viral infection. In some embodiments, the respiratory viral infections are one or more of influenza viral infection (e.g., seasonal flu), rhinovirus infection (e.g., common cold), coronavirus infection (e.g., Severe Acute Respiratory Syndrome and common cold), and/or paramyxovirus infection (e.g., measles). In some embodiments, the coronavirus infection is selected from Severe Acute Respiratory Syndrome-Corona Virus (SARS-CoV), Middle East Respiratory Syndrome virus (CoV-MERS), human HCoV-229E, HCoV-OC43, HCoV-NL63 and HCoV-HKU1. In some embodiments, the coronavirus infection is SARS-CoV (e.g. SARS-CoV-1, SARS-CoV-2). In some embodiments, the SARS-CoV is SARS-CoV-2 (COVID-19). In some embodiments, the respiratory viral infection is an influenza viral infection selected from the group consisting of Influenza A, Influenza B, and Influenza C viral infections. In some embodiments, the Influenza A virus comprises H1N1, H2N2, H3N2, H5N1, H7N7, H1N2, H9N2, H7N2, H7N3, or H10N7 subtypes.

The microorganisms may be air-borne microorganisms (e.g. SARS-Cov-2). In an embodiment the microorganisms are those that cause communicable diseases.

In other embodiments, the compositions of the present disclosure are effective at providing a barrier to common airborne allergens such as pollens, dust mites, molds, animal dander, spores, and the like.

In an embodiment, the barrier-forming compositions and methods of treatment and prevention described herein may be useful, for example, for prevention of infections in environments such as hospitals and infections common in such environments that are contaminated with infectious microorganisms. As mentioned above, the methods and compositions disclosed herein may be especially applicable for immunocompromised patients. In addition, the barrier-forming composition may be useful for prevention of infections by microorganisms that commonly infect wounds.

The contaminated environment may include, for example, a public transportation vehicle, a public gathering place, and a room or vehicle containing a mammal known or expected to be ill, or a close proximity to a mammal known or expected to be ill. More information on environments commonly recognized as contaminated environments, such as an airplane, a nursery, and a health center, is disclosed in Yang, et al., "Concentrations and Size Distributions of Airborne Influenza A Viruses Measured Indoors at a Health Centre, a Day-Care Centre, and on Aeroplanes," J. R. Soc. Interface (Feb. 7, 2011), which is incorporated herein by reference. More specifically, in an embodiment, the public transportation vehicle may be, for example, an airplane, a bus, or a taxi. A public gathering place may be, for example, a doctor's office, a hospital, a school, a nursery, a church, a hotel, or a restaurant. The close proximity to a mammal known or expected to be ill may be, for example, within a one foot radius, or in the same motor vehicle with the mammal. A publicly used airplane may be mentioned as a common and particularly noteworthy example of an environment that many would identify as being a contaminated environment.

In an embodiment, the barrier-forming compositions and methods of treatment and prevention described herein may be useful, for example, for prevention of infections from items that may be contaminated in activity related treatments, such as, for example, ventilator use (which would include medical devices related to the ventilator and contacting the patient).

In an embodiment of the method of preventing an infectious disease, a step includes administering a therapeutically effective amount of a barrier-forming composition to a mucosa of the mammal prior to the mammal encountering the contaminated environment or item. By a therapeutically effective amount, it is meant enough to coat the targeted mucosa with enough of the barrier-forming composition to form a barrier that will result in a barrier layer forming on the mucosa. The barrier-forming compositions of the present disclosure provide a barrier which physically blocks or limits the coated mucosal tissue from exposure to a pathogen or allergen, and/or traps or binds the pathogen/allergen to prevent or reduce exposure to the underlying mucosal tissue. For example, about 50 microliters to about 500 microliters, such as, for example, about 75 microliters to about 200 microliters, such as about 100 microliters to about 150 microliters for a spray formulation. The dosage amount may also be expressed in terms of a volume per square cm, such as, for a spray formulation, for example, about 0.3 to about 2 $\mu L/cm^2$, such as, about 0.625 to about 1 $\mu L/cm^2$. In addition, the average thickness of the film formed on the mucosa from the barrier-forming composition may range, for example, from about 0.001 to about 0.2 mm, such as about 0.01 mm to about 0.1, or about 0.08 to about 0.15 mm. For example, for a given human or animal, the therapeutically effective amount can be determined based on the age or weight or size of the mammal to be treated, and the dosage may be those listed above. For non-human mammals, in particular, the dosage amount may be adjusted according to the per square cm values given above and the approximate surface area of the mucosal surface or body cavity to be treated.

In an embodiment, the barrier-forming compositions of the present disclosure are administered in a therapeutically effective amount to a mucosa and provide a barrier layer on the mucosa that inhibits or prevents the microorganisms from penetrating to the mucosa. In an embodiment, the inhibition of the microorganisms also includes deactivating the microorganism's harmful activity through binding. In an embodiment, the barrier-forming composition blocks all harmful microorganisms contacting the barrier-forming composition. In another embodiment, the barrier substantially blocks enough harmful microorganisms to prevent them from causing an infectious disease. In the latter case, if the harmful microorganism's penetration of the mucosa is slowed and/or diluted it will enhance the body's own ability to prevent the microorganisms from causing disease or widespread infection.

In another embodiment, the barrier-forming compositions of the present disclosure, administered in a therapeutically effective amount to a mucosa, provides a barrier layer on the mucosa that inhibits or prevents allergens from contacting the mucosa. In an embodiment, the barrier-forming composition blocks and/or binds to allergens contacting the barrier-forming composition. In another embodiment, the barrier substantially blocks binds to the allergens sufficiently to prevent them from triggering an allergic reaction, or reduce the severity of the allergic reaction.

In an embodiment, in a continued dosage method of prevention or treatment, the barrier-forming compositions of the present disclosure may be administered in a series of doses, such as, for example, about every 1 to 12 hours, about every 2 to 8 hours, or about every 4 to 6 hours. This method of prevention can be continued, for example, for days, weeks, or months. In some embodiments, the composition is taken on an 'as needed' basis. This continued dosage method may be preferred when the subject is in prolonged contact with a contaminated environment or item.

The mucosa, may, for example, be a mucosal surface in the oral cavity, the nasal cavity, or the pharyngeal cavity, such as, the nasopharynx (epipharynx), the oropharynx (mesopharynx), or the laryngopharynx (hypopharynx). The mucosa may also be in the vaginal cavity, stomach, intestine, throat or other orifices of a mammal, including, but not limited to the ear canal.

In some embodiments, the compositions of the present disclosure are administered by spraying into an oral or nasal orifice of the mammal. In some embodiments, the compositions are administered to both the oral and nasal cavity by spraying into the mouth and exhaling through the nose. Other administration methods include, for example, topically administering the compositions of the present disclosure to the skin or mucosa, e.g., rubbing or applying a gelled barrier-forming composition onto the mucosa or the skin. The barrier-forming composition may be administered to a mammal through many different delivery systems, including, for example: liquids, gels, lubricants, lotions, creams, pastes, aerosolized particles, strips, sprays, rinses, dressings, such as for wound dressings, infusion or layering of the barrier-forming composition into or onto products, such as on condoms, lozenges, or gums. In embodiments, the composition is administered to a mammal as a cream, gel or ointment. In some embodiments, the composition is administered via a nasal pump. Examples of suitable nasal pump sprays include, but are not limited to the Advanced Preservative Free nasal pump spray (Aptar Pharma), Advanced Preservative Free Plus nasal pump spray (Aptar Pharma), VP6 Pump (Aptar Pharma), Advancia nasal pump spray (Nemera), SP270 or SP370 nasal pump sprays (Nemera), or Aero Pump nasal pump spray. In some embodiments, the composition is administered via a RetroNose delivery device as described in U.S. Pat. No. 8,894,604, which is hereby incorporated by reference in its entirety. Other devices for administering the compositions of the present disclosure are breath-actuated pMDIs, throat spray pumps.

In an embodiment, the barrier compositions of the present disclosure may be used to combat transmission of harmful microorganisms by hand-to-mouth or hand-to-nose contact. In such embodiments, the barrier composition is applied to block, trap or neutralize microorganisms introduced into a mammal's oral, nasal, or pharyngeal cavity through the mammals hand-to-mouth or hand-to-nose contact. The method includes identifying a contact with a contaminated item by a hand of the mammal, wherein the contaminated item or environment is known, or expected to be, contaminated with harmful viral, fungal, or bacterial microorganisms. This may include contact with the contaminated items or environment listed above.

Similarly, compositions of the present disclosure can be used to reduce transmission of airborne allergens or pathogens, or transmission of pathogens or allergens to by hand-to-mouth or hand-to-nose contact. In this embodiment, the barrier composition is applied to block or neutralize allergens introduced into a mammal's oral, nasal, or pharyngeal cavity through the mammals hand-to-mouth or hand-to-nose contact. The method includes identifying a contact with a contaminated item by a hand of the mammal, wherein the contaminated item or environment is known, or expected to be, contaminated with harmful allergens. This may include contact with the contaminated items or environment listed above.

Compositions

The present disclosure provides aqueous compositions comprising a mucoadhesive polymer and clay particles. The compositions of the present disclosure are effective for the prevention and treatment of infections (e.g. respiratory infections).

Without being bound by any particular theory, it is believed that when the compositions of the present disclosure cover the mucosal surface, they act as a protective barrier against contact of airborne pathogens and allergens with mucosal cells while also binding or trapping the pathogens or allergens. The clays or phyllosilicates described herein (e.g., bentonite), however, bind both positively charged and negatively charged viruses. It is theorized that sorption and/or binding of a virus to the layered phyllosilicates described herein is achieved by one or more mechanisms selected from the group consisting of adsorption; ionic complexing; electrostatic complexing; chelation; hydrogen bonding; ion-dipole; dipole/dipole; Van Der Waals forces; and any combination thereof. Such ionic bonding, e.g., via one or more cations or negative charge sites of the phyllosilicate sharing electrons with one or two atoms of one or two polar ends of molecules comprising a virus, on a phyllosilicate surface, provides inactivation of a surprisingly high percentage of the viruses. Thus, in various embodiments, clays such as bentonite clay, or montmorillonite clay, interact with the airborne pathogens (e.g. virus, bacteria, fungus) or allergens and effectively inactivate them. The clay particles have pathogen and/or allergen sorption/binding properties due to their negative electrical charge, which binds positively charged pathogens or allergens (such as SARS-Cov-2) and binds them. In addition to acting as a barrier to airborne pathogens, the compositions of the present disclosure are also capable of inactivating pathogens or allergens that are already present on the mucosal surface prior the administration. The bound pathogens or allergens are eliminated from the body via mucociliary clearance.

In some embodiments, the compositions of the present disclosure are thixotropic preparations. The term "thixotropic preparation" is to be understood to mean such that feature, when subjected to shear forces (shaking, pressing through a nozzle, stirring, or the like), a low viscosity (sol state), suitable in particular for use as nose drops or in particular as a nasal spray, for preference in the range from $8.90 \times 10^{-4}$ Pa*s to 00.015, in particular from $8.90 \times 10^{-4}$ to 0.007 Pa*s (=kg/(m×s)), while by contrast when in a state of rest feature a high viscosity, for preference in the range from 0.015 to 1000 Pa*s. The measurement is effected 0.015 to 1000 Pa*s. The measurement is performed by means of a rotational viscometer, or other viscometry methods known in the art. An advantage of formulating the compositions as a thixotropic preparation is their ease of use. For, example, in contrast to thermosensitive gels no defined temperatures are required before administration. Simple shaking or pumping allows to bring them into the sol state appropriate for administration (e.g. via a nasal delivery device).

In some embodiments, the compositions of the present disclosure possess shear thinning properties. The term "shear-thinning" refers to the rheological viscoelastic properties of a material related to fluid-like or non-fluid-like behavior and flow. Shear stress and shear-thinning include properties related to Bingham flow, plastic flow, pseudoplasticity, dilatancy, thixotropy, rheopexy, and the like or other stress and/or strain properties of a viscous material. Further, "shear-thinning" refers to a reduction in apparent viscosity (the ratio of shear stress to the shear rate) with increasing (pseudoplastic), time dependent (thixotropic) or associated with a yield stress, defined as a stress that must be exceeded before flow starts, (Bingham plastics and generalized Bingham plastics). See generally, Harris, J., & Wilkinson, W. L., "Non-Newtonian Fluid," pp. 856-858 in Parker, S. P., ed., McGraw-Hill Encyclopedia of Physics, Second Edition, McGraw-Hill, New York, 1993.

In some embodiments of the present disclosure, the composition can be formulated in any form suited for administration by various pathways including nasally (e.g., solution, spray, drops, aerosol, gels, dry powders), orally (e.g., topically (e.g., spray, solution, drops, aerosol, gels, dry powders, drug-releasing skin patch, cream or ointment), intravaginally, by drench, transdermally, intradermally, pulmonary, by intra-uterine patch or device, by the use of an aerosol).

The mucoadhesive polymer(s) is/are present at a level of from about 0.1% to about 3% by weight of the composition. For example, the mucoadhesive polymer(s) may be present at about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, or about 3.0%. The mucoadhesive polymer may range from about 0.1% to about 3%, about 0.1% to about 2.5%, about 0.1% to about 2.0%, about 0.1% to about 1.5%, about 0.1% to about 1.0%, about 0.1% to about 0.8%, about 0.1% to about 0.6%, about 0.2% to about 3%, about 0.2% to about 2.5%, about 0.2% to about 2.0%, about 0.2% to about 1.5%, about 0.2% to about 1.0%, about 0.2% to about 0.8%, about 0.2% to about 0.6%, about 0.3% to about 3%, about 0.3% to about 2.5%, about 0.3% to about 2.0%, about 0.3% to about 1.5%, about 0.3% to about 1.0%, about 0.3% to about 0.8%, about 0.3% to about 0.6%, about 0.3% to about 0.5%, about 0.4% to about 3%, about 0.4% to about 2.5%, about 0.4% to about 2.0%, about 0.4% to about 1.5%, about 0.4% to about 1.0%, about 0.4% to about 0.8%, about 0.4% to about 0.6%, about 0.6% to about 2.8%, about 0.6% to about 2.6%, about 0.8% to about 2.6%, about 0.8% to about 2.4%, about 0.8% to about 2.2%, about 0.8% to about 1.8%, about 0.8% to about 1.6%, about 0.8% to about 1.4%, about 0.8% to about 1.2%, about 1.0% to about 2.0%, about 1.0% to about 1.8%, about 1.0% to about 1.6%, about 1.0% to about 1.4%, about 1.0% to about 1.2%, about 1.2% to about 2.0%, about 1.2% to about 1.8%, about 1.2% to about 1.6%, about 1.2% to about 1.4%, about 1.4% to about 2.0%, about 1.4% to about 1.8%, about 1.4% to about 1.6%, about 1.6% to about 2.0%, or about 1.6 to about 1.8%. In embodiments, the mucoadhesive polymer (e.g., xanthan gum) is about 0.1% to about 0.5% by weight of the composition. In embodiments, the mucoadhesive polymer (e.g., xanthan gum) is about 0.2% by weight of the composition.

The clay is present at a level of from about 0.4% to about 5% by weight of the composition. For example, the clay may be present at about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, about 3.0%, about 3.1%, about 3.2%, about 3.3%, about 3.4%, about 3.5%, about 3.6%, about 3.7%, about 3.8%, about 3.9%, about 4.0%, about 4.1%, about 4.2%, about 4.3%, about 4.4%, about 4.5%, about 4.6%, about 4.7%, about 4.8%, about 4.9%, or about 5.0%. For example, the clay (e.g., bentonite clay) may be present at about 2.5% by weight of the composition. The clay may range from about 0.4% to about 3%, about 0.4% to about 2.8%, about 0.4% to about 2.5%, about 0.6% to about 3%, about 0.6% to about 2.8%, about 0.6% to about 2.6%, about 0.8% to about 2.6%, about 0.8% to about 2.4%, about 0.8% to about 2.2%, about 0.8% to about 2.2%, about 0.8% to about 1.8%, about 0.8% to about 1.6%, about 0.8% to about 1.4%, about 0.8% to about 1.2%, about 1.0% to about 2.0%, about 1.0% to about 1.8%, about 1.0% to about 1.6%, about 1.0% to about 1.4%, about 1.0% to about 1.2%, about 1.2% to about 2.0%, about 1.2% to about 1.8%, about 1.2% to about 1.6%, about 1.2% to about 1.4%, about 1.4% to about 2.0%, about 1.4% to about 1.8%, about 1.4% to about 1.6%, about 1.6% to about 2.0%, about 1.6 to about 1.8%, about 2% to about 4%, about 2% to about 3.8%, about 2% to about 3.6%, about 2% to about 3.4%, about 2% to about 3.2%, about 2% to about 3%, about 2% to about 2.8%, about 2% to about 2.6%, about 2% to about 2.4%, about 2% to about 2.2%, about 2.4% to about 4%, about 2.4% to about 3.8%, about 2.4% to about 3.6%, about 2.4% to about 3.4%, about 2.4% to about 3.2%, about 2.4% to about 3%, about 2.4% to about 2.8%, about 2.4% to about 2.6%, about 2.8% to about 4%, about 2.8% to about 3.8%, about 2.8% to about 3.6%, about 2.8% to about 3.4%, about 2.8% to about 3.2%, about 2.8% to about 3%, about 3% to about 4%, about 3% to about 3.8%, about 3% to about 3.6%, about 3% to about 3.4%, about 3% to about 3.2%, about 0.5% to about 5%, about 1% to about 5%, about 2% to about 5%, about 3% to about 5%, about 4% to about 5%, about 4.2% to about 5%, or about 4.5% to about 5%. For example, the clay (e.g., bentonite clay) may range from about 2.0% to about 3.0% by weight of the composition. Clays are composed of fine particles of clay minerals that are layer-type hydrous (containing structural hydroxyl groups) silicates of aluminum, magnesium, potassium, iron, and other less abundant elements, particularly alkalis and alkaline earth metals. In some embodiments, the clays are silicates of aluminum, magnesium and iron. For example, magnesium aluminum silicate (or aluminum magnesium silicate), occurring naturally in such smectite minerals as colerainite, saponite, and sapphirine. Refined magnesium aluminum silicates useful herein are readily available as Veegum, manufactured by R. T. Vanderbilt Company, Inc. Reference to "clay" herein refers to a single type of clay, but also includes mixtures of two or more different forms of clays described herein.

Clay may also contain varying amounts of non-clay minerals such as quartz, calcite, feldspar, and pyrite. Preferred clays useful herein are water swellable clays.

The term "clay" as used herein includes but is not limited to kaolin minerals such as kaolinite, china clay, dickite, nacrite, halloysite; serpentine minerals such as lizardite, halloysite, chrysotile, antigorite, carlosturanite, amestite, cronstedite, chamosite, berthierine, garierite; talc; pyrophyllite; ferripyrophyllite; smectites such as montmorillonites, beidellite, nontronite, hectorite, saponite, sauconite, medmontite, pimelite, bentonite; illite minerals such as ledikete, bravaisite, degraded mica, hydromica, hydromuscovite, hydrous illite, hydrous mica, K-mica, micaceous clay, and sericite; mica such as pegmatite, muscovite, and phlogopite; brittle mica such as margarite, and clintonite; glauconite; celadonite; chlorite and vermiculite such as pennine, clinochlore, chamosite, nimite, baileychlore, donbassite, cookite, sudoite, franklinfurnaceite; palygorskite and sepiolite minerals such as attapulgite; allophane and imogolite; mixed layer clay minerals such as talc-chlorite; and mixtures thereof.

In some embodiments, the clays are selected from the group consisting of kaolin minerals, smectites, mica, and mixtures thereof. For example, the clay may be laponite, bentonite, hectorite, saponite, montmorillonites, and mixtures thereof. In some embodiments, the clay is bentonite. In some embodiments, the bentonite is sodium bentonite. In some embodiments, the bentonite is calcium bentonite. In some embodiments, the bentonite is a mixture of sodium bentonite and calcium bentonite.

Any of the available forms are acceptable for use in the present invention such as colloidal clays, for example magnesium aluminosilicate, magnesium bentonite, attapulgite, sodium bentonite magma, etc.

Clays that are useful in the present invention include both mined, naturally occurring clays as well as synthetic clays. The clays must be pharmaceutically acceptable. A more detailed description of the clays and clay minerals useful herein can be found in the following three references, each of which is incorporated by reference in its entirety: Kirk-Othmer, *Encyclopedia of Chemical Technology*, Fourth Edition, Vol. 6, pages 381-423; Dell, D. J., "Smectite Clays in Personal Care Products", *Cosmetics& Toiletries*, Vol. 108, May 1993, pages 79-85; and Theng B. K. G., "Formation and Properties of Clay-Polymer Complexes", *Developments in Soil Science*, Vol. 9. Clays include products available from Southern Clay Products, Gonzalez, Tex.; Generichem, Totowa, N.J.; R. T. Vanderbilt, Norwalk, Conn.; Smeotite, Inc., Casper, N.Y.

In some embodiments, the composition comprises one or more viscosity agents or one or more pharmaceutically acceptable viscosity enhancing agents. Non limiting examples of suitable viscosity agents or viscosity enhancing agents include caprylic/capric triglyceride (e.g. Miglyol 812N), glyceryl stearate (e.g. geleol mono and diglycerides), xanthan gum (e.g. XANTURAL 180), polyvinyl pyrrolidone, polyvinyl alcohol, methylcellulose, carboxymethyl cellulose-Na, hydroxyethylcellulose, hydroxypropyl cellulose, hydroxypropyl methylcellulose, polyethylene-oxide, Carbopol, polyethylene glycol, propylene glycol, glycerin, alginates, carrageenan pectins, maltodextrin, sodium starch glycolate, tragacanth gum, gum arabic, microcrystalline cellulose and derivatives thereof. In some embodiments, the viscosity enhancing agent is one or more of caprylic/capric triglyceride (e.g. Miglyol 812N), glyceryl stearate (e.g. geleol mono and diglycerides), and xanthan gum (e.g. XANTURAL 180). In some embodiments, the viscosity enhancing agent is polyvinyl pyrrolidone or hydroxypropyl methylcellulose (HPMC). In some embodiments, the composition of the present disclosure comprises one or more viscosity agents and is an intranasal composition. In some embodiments, the one or more viscosity agents, in combination with the mucoadhesive polymers, allows the formulation to be retained on the mucosa long enough to sufficiently prevent infection. For example, the composition may be retained on the mucosal surface for greater than about 5 minutes, about 10 minutes, about 15 minutes, about 20 minutes, about 25 minutes, about 30 minutes, about 45 minutes, about 1 hour, about 1 and a half hour, about 2 hours, about 2 and a half hours, about 3 hours, about 4 hours, about 5 hours, about 6 hours, about 7 hours, about 8 hours, about 9 hours, about 10 hours, about 11 hours, about 12 hours, about 16 hours, about 20 hours, or about 24 hours. In some embodiments, the presence of one or more viscosity agents in the formulation for intranasal administration does not prevent the formulation to be sprayed into the nasal cavity.

The one or more viscosity agents or one or more pharmaceutically acceptable viscosity enhancing agents are present at a level of from about 0.1% to about 50% by weight of the composition. For example, the one or more viscosity agents or one or more pharmaceutically acceptable viscosity enhancing agents may be present at about 0.1%, about 0.2%, about 0.3%, about 0.4%, about 0.5%, about 0.6%, about 0.7%, about 0.8%, about 0.9%, about 1.0%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, or about 50%. For example, the one or more viscosity agents may be present at about 1.5% by weight of the composition. The one or more viscosity agents or one or more pharmaceutically acceptable viscosity enhancing agents may range from about 0.1% to about 50%, about 0.1% to about 25%, about 0.1% to about 10%, about 0.1% to about 5%, about 10% to about 50%, about 10% to about 40%, about 10% to about 35%, about 10% to about 30%, about 10% to about 20%, about 15% to about 50%, about 15% to about 40%, about 15% to about 35%, about 15% to about 30%, about 15% to about 25%, about 15% to about 20%, about 20% to about 50%, about 20% to about 45%, about 20% to about 40%, about 20% to about 35%, about 20% to about 30%, about 20% to about 25%, about 25% to about 50%, about 25% to about 45%, about 25% to about 40%, about 25% to about 35%, about 25% to about 35%, about 25% to about 30%, about 30% to about 50%, about 30% to about 45%, about 30% to about 40%, about 30% to about 35%, about 35% to about 50%, about 35% to about 45%, about 35% to about 40%, about 40% to about 50%, about 40% to about 45%, or about 45% to about 50. For example, the one or more viscosity agents may be present at about 0.1% to about 10%, about 0.1% to about 5%, about 0.5% to about 2.5%, or about 1% to about 2% by weight of the composition.

In some embodiments, the viscosity of the compositions described herein is measured by the USP <911> Viscosity method.

In some embodiments, the viscosity of the compositions described herein is measured by the European Pharmacopeia method such as that described at Ph. Eur. 2.2.8.

In some embodiments, the compositions of the present disclosure have an osmolality in the range of about 200 mOsm/kg to about 1500 mOsm/kg or about 400 mOsm/kg to about 1200 mOsm/kg. In some embodiments, the osmolality of the composition of the present disclosure is about 200 mOsm/kg, about 300 mOsm/kg, about 400 mOsm/kg, about 500 mOsm/kg, about 600 mOsm/kg, about 700 mOsm/kg, about 800 mOsm/kg, about 900 mOsm/kg, about 1000 mOsm/kg, about 1100 mOsm/kg, about 1200 mOsm/kg, about 1300 mOsm/kg, about 1400 mOsm/kg, about 1500 mOsm/kg, about 1600 mOsm/kg, about 1700 mOsm/kg, about 1800 mOsm/kg, about 1900 mOsm/kg, about 2000 mOsm/kg, about 2100 mOsm/kg, about 2200 mOsm/kg, about 2300 mOsm/kg, about 2400 mOsm/kg, or about 2500 mOsm/kg.

In some embodiments, the compositions of the present disclosure have an osmolality in the range of about 200 mOsm/kg to about 600 mOsm/kg, about 400 mOsm/kg to about 1000 mOsm/kg, about 500 mOsm/kg to about 2000 mOsm/kg, about 500 mOsm/kg to about 1500 mOsm/kg, about 500 mOsm/kg to about 1000 mOsm/kg, about 1000 mOsm/kg to about 2000 mOsm/kg, about 1000 mOsm/kg to about 1600 mOsm/kg, about 1200 mOsm/kg to about 1800 mOsm/kg, about 1500 mOsm/kg to about 1800 mOsm/kg, about 1500 mOsm/kg to about 2000 mOsm/kg.

In some embodiments, the osmolality of the compositions described herein is measured by the USP <785> Osmolality method. In some embodiments, the osmolality of the compositions described herein is measured by the European Pharmacopeia method such as that described at Ph. Eur. 2.2.35.

In some embodiments, the osmolality of the compositions described herein is measured by the cryoscopy method that measures the freezing point depression of the test solution. An osmometer for freezing point depression measurement comprises a means for cooling the container used for the measurement; a resistor sensitive to temperature (thermistor), with an appropriate current- or potential-difference measurement device that may be graduated in temperature change or in osmolality; and a means for mixing the sample. First, the osmometer is calibrated according to the manufacturer's instructions. The osmometer calibration is confirmed with at least two standard solutions such that the osmolalities of the standard solutions span the expected range of osmolality of the test solution. The osmometer reading should be within ±2 mOsmol/kg from the standard solution. For calibration, an appropriate volume of the standard solution is introduced into the measurement cell as per the manufacturer's instructions, and the cooling system is started. The mixing device is generally programmed to operate at a temperature below the lowest temperature expected from the freezing point depression. The apparatus indicates when the equilibrium is attained. The osmometer is calibrated using an appropriate adjustment device such that the reading corresponds to either the osmolality or freezing point depression value of the standard solution. Some instruments indicate osmolality and some others show freezing point depression. Before each measurement, the measurement cell is rinsed at least twice with the solution to be tested. The procedure is repeated with the test solution.

In some embodiments, the compositions of the present disclosure comprise one or more lipophilic additives or excipients. If employed, the lipophilic excipients may be an emollient, such as emollients known in the art. In some embodiments, the compositions of the present disclosure exclude lipophilic additives such as oils, fatty esters, fatty acids, or fatty alcohols. In other embodiments, the compositions of the present disclosure include oils, fatty esters, fatty acids, or fatty alcohols, such as diisopropyl adipate, diisopropyl sebacate, triethyl citrate, isopropyl myristate, isopropyl palmitate, myristyl propionate, 2-ethylhexyl palmitate, cetyl palmitate, cetyl stearate, triglycerides, fatty acids, fatty acid esters, fatty alcohols (e.g. an oleyl alcohol), and combinations thereof. A suitable triglyceride is caprylic/capric triglyceride and a suitable fatty acid is caprylic acid. In some embodiments, the lipophilic excipient is caprylic/capric triglyceride (Miglyol 812 N). In some embodiments, the lipophilic excipient is one or more oils selected from (i) hydrocarbons, e.g. mineral oils, in particular paraffin, paraffin oil (in particular white paraffin oil, low-viscosity or in a broader embodiment high-viscosity paraffin oil), purcellin oil or perhydrosqualene, or further hard paraffin or vaseline; or (ii) Vegetable oils, e.g. almond oil, groundnut oil, wheatgerm oil, rape oil, linseed oil, cottonseed oil, apricot oil, walnut oil, palm oil, pistachio oil, sesame oil, poppyseed oil, pine oil, castor oil, soya oil, avocado oil, cocoa oil, hazelnut oil, olive oil, grapeseed oil, rice oil, safflower oil, maize germ oil, peach-kernel oil, coffee oil, Jojoba oil, sunflower oil, thistle oil, cocoa butter or the like, or the hydrated, polyoxyethylated, polyoxy- or hydrated polyoxyderivatives or fractionated derivatives thereof. In some embodiments, the oil is an animal oil, saturated or non-saturated ester, higher alcohols and/or silicone oils, or mixtures of two or more of these components. The one or more lipophilic excipients are present at a level of from about 0.1% to about 50% by weight of the composition. For example, the lipophilic excipient may be present at about 0.1%, about 0.2%, about 0.3%, about 0.4%, about 0.5%, about 0.6%, about 0.7%, about 0.8%, about 0.9%, about 1.0%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, or about 50%. For example, the lipophilic excipient (e.g., caprylic/capric triglyceride) may be present at about 35% by weight of the composition. The one or more lipophilic excipients may range from about 0.1% to about 50%, about 0.1% to about 25%, about 0.1% to about 10%, about 0.1% to about 5%, about 10% to about 50%, about 10% to about 40%, about 10% to about 35%, about 10% to about 30%, about 10% to about 20%, about 15% to about 50%, about 15% to about 40%, about 15% to about 35%, about 15% to about 30%, about 15% to about 25%, about 15% to about 20%, about 20% to about 50%, about 20% to about 45%, about 20% to about 40%, about 20% to about 35%, about 20% to about 30%, about 20% to about 25%, about 25% to about 50%, about 25% to about 45%, about 25% to about 40%, about 25% to about 35%, about 25% to about 35%, about 25% to about 30%, about 30% to about 50%, about 30% to about 45%, about 30% to about 40%, about 30% to about 35%, about 35% to about 50%, about 35% to about 45%, about 35% to about 40%, about 40% to about 50%, about 40% to about 45%, or about 45% to about 50. For example, the lipophilic excipient (e.g., caprylic/capric triglyceride) may range from about 30% to about 40% by weight of the composition.

In some embodiments, the compositions of the present disclosure comprise one or more pharmaceutically acceptable moisturizing agents. Non-limiting examples of such moisturizing agents include glycerin, ethylene glycol, propylene glycol, propylene glycol 400, polyethylene glycol 400, hexalene glycol, butylene glycol, dextrose, glyceryl triacetate, polydextrose, glycerol, glyceryl triacetate, sorbitol, and mannitol. In various embodiments, the compositions of the present disclosure can include mixtures of pharmaceutically acceptable moisturizing agents. The one or more moisturizing agents are present at a level of from about 0.1% to about 10% by weight of the composition. For example, the one or more moisturizing agents may be present at about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, about 3.0%, about 3.1%, about 3.2%, about 3.3%, about 3.4%, about 3.5%, about 3.6%, about 3.7%, about 3.8%, about 3.9%, about 4.0%, about 4.1%, about 4.2%, about 4.3%, about 4.4%, about 4.5%, about 4.6%, about 4.7%, about 4.8%, about 4.9%, about 5.0%, about 5.1%, about 5.2%, about 5.3%, about 5.4%, about 5.5%, about 5.6%, about 5.7%, about 5.8%, about 5.9%, about 6.0%, about 6.1%, about 6.2%, about 6.3%, about 6.4%, about 6.5%, about 6.6%, about 6.7%, about 6.8%, about 6.9%, about 7.0%, about 7.1%, about 7.2%, about 7.3%, about 7.4%, about 7.5%, about 7.6%, about 7.7%, about 7.8%, about 7.9%, about 8.0%, about 8.1%, about 8.2%, about 8.3%, about 8.4%, about 8.5%, about 8.6%, about 8.7%, about 8.8%, about 8.9%, about 9.0%, about 9.1%, about 9.2%, about 9.3%, about 9.4%, about 9.5%, about 9.6%, about 9.7%, about 9.8%, about 9.9%, or about 10.0%. For example, the moisturizing agent may be present at about 5.0% by weight of the composition. The one or more moisturizing agents may range from about 0.1% to about 3%, about 0.10% to about 2.8%, about 0.10% to about 2.5%, about 0.2% to about 3%, about 0.2% to about 2.8%, about 0.2% to about 2.5%, about 0.3% to about 3%, about 0.3% to about 2.8%, about 0.3% to about 2.5%, about 0.4% to about 3%, about 0.4% to about 2.8%, about 0.4% to about 2.5%, about 0.6% to about 3%, about 0.6% to about 2.8%, about 0.6% to about 2.6%, about 0.8% to about 2.6%, about 0.8% to about 2.4%, about 0.8% to about 2.2%, about 0.8% to about 2.2%, about 0.8% to about 1.8%, about 0.8% to about 1.6%, about 0.8% to about 1.4%, about 0.8% to about 1.2%, about 1.0% to about 3.0%, about 1.0% to about 2.8%, about 1.0% to about 2.3%, about 1.0% to about 2.0%, about 1.0% to about 1.8%, about 1.0% to about 1.6%, about 1.0% to about 1.4%, about 1.0% to about 1.2%, about 1.2% to about 3.0%, about 1.2% to about 2.8%, about 1.2% to about 2.6%, about 1.2% to about 2.4%, about 1.2% to about 2.2%, about 1.2% to about 2.0%, about 1.2% to about 1.8%, about 1.2% to about 1.6%, about 1.2% to about 1.4%, about 1.4% to about 3.0%, about 1.4% to about 2.8%, about 1.4% to about 2.6%, about 1.4% to about 2.4%, about 1.4% to about 2.2%, about 1.4% to about 2.0%, about 1.4% to about 1.8%, about 1.4% to about 1.6%, about 1.6% to about 3.0%, about 1.6% to about 2.8%, about 1.6% to about 2.6%, about 1.6% to about 2.4%, about 1.6% to about 2.2%, about 1.6% to about 2.0%, about 1.6 to about 1.8%, about 1.8% to about 3.0%, about 1.8% to about 2.8%, about 1.8% to about 2.6%, about 1.8% to about 2.4%, about 1.8% to about 2.2%, about 1.8% to about 2.0%, about 2% to about 3.0%, about 2% to about 2.8%, about 2% to about 2.6%, about 2% to about 2.4%, about 2% to about 2.2%, about 2.2% to about 3.0%, about 2.2% to about 2.8%, about 2.2% to about 2.6%, about 2.2% to about 2.4%, about 2.4% to about 3.0%, about 2.4% to about 2.8%, about 2.4% to about 2.6%, about 2.6% to about 3.0%, about 2.6% to about 2.8%, about 2.8% to about 3%, about 1% to about 5%, about 2% to about 5%, about 3% to about 5%, about 4% to about 5%, about 4.2% to about 5%, about 4.5% to about 5%, about 3% to about 10%, about 4% to about 10%, about 3% to about 6%, about 4% to about 6%, about 5% to about 10%, about 5% to about 8%, about 5% to about 7%, about 6% to about 10%, about 6% to about 8%, or about 8% to about 10%. For example, the moisturizing agent may range from about 1% to about 10%, about 2.5% to about 7.5%, or about 4% to about 6% by weight of the composition.

In some embodiments, the one or more moisturizing agents are selected from glycerin, polyethylene glycol 400 and propylene glycol. In some embodiments, the compositions of the present disclosure comprise glycerin. In some embodiments, the composition of the present disclosure comprises polyethylene glycol 400. In some embodiments, the composition of the present disclosure comprises propylene glycol. In some embodiments, the compositions of the present disclosure comprise glycerin, polyethylene glycol 400 and propylene glycol. In embodiments, the moisturizing agents are propylene glycol and mannitol.

In some embodiments, the compositions of the present disclosure comprising one or more pharmaceutically acceptable moisturizing agents are intranasal compositions. In some embodiments, one or more moisturizing agents in the intranasal composition for intranasal administration moisturize the nasal mucosa, nasal tissues, and/or nasal membrane. In some embodiments, one or more moisturizing agents in the intranasal composition for intranasal administration reduce irritation in the nasal cavity after administration and improve tolerance. In some embodiments, the intranasal composition of the present disclosure comprises glycerin, polyethylene glycol 400 and propylene glycol.

In some embodiments, the compositions of the present disclosure comprise one or more pharmaceutically acceptable carriers and/or one or more pharmaceutically acceptable excipients.

In some embodiments, the compositions of the present disclosure further comprise one or more additives, including but not limited to, preservatives, agents influencing osmolarity, complexing agents (such as, for example, sodium edetate), surfactants, agents which influence the pH and tonicity, and sensory masking agents. In some embodiments, the composition of the present disclosure for intranasal delivery further comprises one or more additives, including but not limited to, preservatives, agents influencing osmolarity, complexing agents (such as, for example, sodium edetate), surfactants, agents which influence the pH and tonicity, and sensory masking agents.

Non-limiting examples of additives and/or excipients include benzyl alcohol, benzalkonium chloride, carboxymethyl cellulose sodium/cellulose microcrystalline, propylparaben, methylparaben, phenethyl alcohol, chlorobutanol, EDTA, ethanol, ascorbic acid, hydrochloric acid, sulfuric acid, sodium hydroxide, potassium phosphate, sodium phosphate, sodium citrate, sodium chloride, anhydrous dextrose, butylated hydroxyanisole, butylated, hydroxytoluene, PEG 400, PEG 3500, polyoxyl 400 stearate, polysorbate 20, polysorbate 80, glycerin, propylene glycol, glyceryl triacetate, glycerol, ethylene glycol, sorbitol, mannitol, and alginates, carrageenan pectins, tragacanth gum, gum arabic.

The composition disclosed herein can be formulated in accordance with the routine procedures adapted for desired administration route. Suitable formulations for each of these methods of administration can be found, for example, in Remington: The Science and Practice of Pharmacy, A. Gennaro, ed., 20th edition, Lippincott, Williams & Wilkins, Philadelphia, PA.

In some embodiments, pharmaceutically acceptable carriers are well known to those skilled in the art and include, but are not limited to, buffer solutions, saline, and water. In some embodiments, a pharmaceutically acceptable carrier includes about 0.01 to about 0.1 M phosphate buffer or saline (e.g., 0.8% saline). In some embodiments, the buffer solution comprises a citric acid buffer. The citric acid buffer may be, for example a 1M solution. In some embodiments, the buffer solution comprises sodium phosphate dibasic and sodium phosphate monobasic. In some embodiments, the buffer solution comprises sodium phosphate dibasic, sodium phosphate monobasic, and trisodium citrate dihydrate. In some embodiments, buffering agents are selected from the group consisting of sodium phosphate dibasic, sodium phosphate monobasic, trisodium citrate dihydrate, sodium chloride, potassium chloride, potassium dihydrogen phosphate, HEPES, potassium metaphosphate, potassium phosphate, monobasic sodium acetate, sodium bicarbonate, tris, sodium tartrate, sodium citrate anhydrous and dihydrate, and a combination thereof. For example, pH can be controlled to fall within a range of about 4 to about 9, including pH values of about 4, about 4.2, about 4.4, about 4.5, about 4.8, about 5, about 5.2, about 5.4, about 5.5, about 5.6, about 5.8, about 6, about 6.2, about 6.4, about 6.8, about 7, about 7.2, about 7.4, about 7.6, about 7.8, about 8, about 8.2, about 8.4, about 8.6, about 8.8, or about 9, inclusive of all ranges between any of these values. In some embodiments, the composition of the present disclosure has a pH value of about 4.5 to about 7. In some embodiments of any of the compositions described herein, the composition has a pH value of about 4.5 to about 7, including about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, to about 7.0, including all values and subranges therebetween. In embodiments, citric acid is added until the composition has a pH of about 5 to about 7, or about 6 to about 7. In embodiments, citric acid is added until the composition has a pH of about 5. In embodiments, citric acid is added until the composition has a pH of about 5 to about 7.

In some embodiments, pharmaceutically acceptable carriers can be aqueous or non-aqueous solutions, suspensions and emulsions. Examples of non-aqueous solvents suitable for use in the present application include, but are not limited to, propylene glycol, polyethylene glycol, vegetable oils such as olive oil, and injectable organic esters such as ethyl oleate.

Aqueous carriers suitable for use in the present application include, but are not limited to, water, alcoholic/aqueous solutions (such as ethanol/water), glycerol and or glycerol/aqueous mixtures, emulsions or suspensions, including saline and buffered media. Oral carriers can be elixirs, syrups, capsules, tablets and the like.

Liquid carriers suitable for use in the present application can be used in preparing solutions, suspensions, or emulsions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators.

Liquid carriers suitable for use in the present application include, but are not limited to, water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). If the compositions of the present invention are administered from pressurized containers (e.g., pressurized, metered dose dispensers), the liquid carrier for pressurized compositions disclosed herein can be a halogenated hydrocarbon, hydrocarbon, carbon dioxide, or other pharmaceutically acceptable propellant.

Flavoring agents and flavor enhancers may make the dosage form more palatable to the patient, in the event that some of the intranasally administered composition is ingested. Common flavoring agents and flavor enhancers for pharmaceutical products that may be included in the composition and/or combination of the present invention include maltol, vanillin, ethyl vanillin, menthol, citric acid, fumaric acid, ethyl maltol, tartaric acid, mint, camphor, eucalyptus, and the like.

The compositions of the present disclosure may also comprise a signaling agent. The signaling agent allows a user to sense administration of the composition. For example, the signaling agent may be mint, spearmint, peppermint, eucalyptus, lavender, citrus, lemon, lime, or any combination thereof. The inclusion of such flavoring or signaling agents in the composition can provide the patient with pleasant sensory feedback upon use, which allows the patient to recognize that administration has occurred, and may aid the patient's recollection of administration. Such factors can improve patient compliance and provide a positive psychological effect. It has also been found that including a flavoring/signaling agent enhances the prophylactic or therapeutic effect of powder compositions of the present invention. More specifically, compositions including mint, menthol and the like are thought to be more effective at treating allergic rhinitis and asthma than compositions of the invention which do not include a signaling agent.

Sensory masking agents can be used to taste mask and/or odor mask sensation in connection with the administration of the composition. In some embodiments, the odor masking agent can include a scented aromatic masking agent. In some embodiments, any known sensory masking agents which is known in the pharmaceutical literature can be considered. Exemplary taste-masking agents include, but are not limited to, sucralose, aspartame, lactose, sorbitol, saccharin, sodium saccharin, sucrose, fructose, mannitol, invert sugar, citric acid, and sodium citrate.

Compositions of the present disclosure may also include a dye using any pharmaceutically acceptable colorant to improve their appearance and/or facilitate patient identification of the product and unit dosage level in liquid compositions of the present invention where the components are dissolved or suspended in a liquid carrier such as water, vegetable oil, alcohol, polyethylene glycol, propylene glycol, or glycerin.

For example, formulations for inhalation administration contain as excipients, for example, lactose, or can be aqueous solutions containing, for example, polyoxyethylene-9- auryl ether, glycocholate and deoxycholate, or oily solutions for administration in the form of nasal drops, or as a gel to be applied intranasally. Formulations for parenteral administration can also include glycocholate for buccal administration, methoxysalicylate for rectal administration, or citric acid for vaginal administration.

Liquid compositions and/or combinations may contain emulsifying agents to disperse uniformly throughout the composition and/or combination an active ingredient or other excipient that is not soluble in the liquid carrier. Emulsifying agents that may be useful in liquid compositions and/or combinations of the present invention include, for example, gelatin, egg yolk, casein, cholesterol, acacia, tragacanth, chondrus, pectin, methyl cellulose, carbomer, cetostearyl alcohol, and cetyl alcohol.

Sweetening agents such as aspartame, lactose, sorbitol, saccharin, sodium saccharin, sucrose, fructose, mannitol, and invert sugar may be added to improve the taste.

The compositions of the present disclosure may also comprise preservatives, co-preservatives, and chelating agents. For example, the preservatives, co-preservatives, and chelating agents may include alcohols, quaternary ammonium compounds such as benzethonium chloride, benzoxonium chloride, benzododecinium bromide, alkyltrimethilammonium bromide, cetrimonium bromide, benzalkonium chloride, phenylethyl alcohol, benzoic acid and esters and salts thereof, e.g. sodium benzoate, C1-C$_7$-alkyl esters of 4-hydroxybenzoic acid, such as methyl 4-hydroxybenzoate, sodium methyl 4-hydroxybenzoate or propyl 4-hydroxybenzoate, butylated hydroxyl toluene, butylated hydroxyanisole, cetylpyridinium chloride, cetrimide; parabens and derivatives such as propylparaben or methylparaben; alkyl acids, such as potassium sorbate, sorbic acid, calcium sorbate, sodium sorbate; biguanides, e.g. chlorhexidine or nasally acceptable salts thereof, e.g. chlorhexidine digluconate, chlorhexidine acetate or chlorhexidine chloride, 2-phenoxyethanol, Euxyl 9010 (phenoxyethanol and ethylhexylglycerin 9:1); hydroxyacetophenone (e.g. SY979940 SymSave® H), 1,2-pentanediol (SY996442 Hydrolite® 5 green), SY973949 SymOcide® PH (phenoxyethanol (~72%), hydroxyacetophenone (17.5%), caprylyl glycol (7.5%)), caprylyl glycol alone or in combination with other preservatives or co-preservatives (e.g. SY973949 SymOcide® PH), ethylhexylglycerine alone or in combination with other preservatives or co-preservatives (e.g. Euxyl 9010), boric acids; phenols such as 4-chlorocresol, 4-chloroxylenol, dichlorophene or hexachlorophene and chelators such as ethylenediamine tetraacetic acid (EDTA), disodium EDTA (e.g. sodium edetate TITRIPLEX III) or ethylenediamine-N,N'-disuccinic acid (EDDS) may be added at levels safe for administration to improve storage stability. In some embodiments, the preservatives or co-preservatives may be an anti-oxidant. Suitable antioxidants include, include, but are not limited to, butylated hydroxyanisole, butylated hydroxytoluene, malic acid, ascorbyl palmitate, retinyl palmitate, sodium ascorbate, sodium metabisulphite, propyl gallate, beta-carotene, ascorbic acid, sodium ascorbyl phosphate, magnesium ascorbyl phosphate, ascorbic acid-2-glycoside, ascorbyl palmitate, hydroxyacetophenone, ascorbyl stearate, α-lipoic acid, glutathione, coenzyme Q10, tocopherols (e.g. alpha, beta, gamma, delta), tocopherol acetate, retinol, retinol palmitate, genistein, quercetin, epigallocatechin, epigallocatechin gallate, gallocatechin gallate, sylibin, diosmetin, kaempferol, epicatechin, galangin, indolic acid, γ-linolenic acid, linoleic acid, chlorogenic acid, tocotrienol, astaxanthin, and any pharmaceutically acceptable salts thereof, any analogues thereof and any combination of the foregoing. In some embodiments, the composition comprises benzalkonium chloride as a preservative. In some embodiments, the composition comprises methyl paraben as a preservative. In some embodiments, the composition is free of benzalkonium chloride.

The one or more preservatives and chelating agents are present at a level of from about 0.01% to about 3% by weight of the composition. For example, the one or more preservatives and chelating agents may be present at about 0.01%, about 0.02%, about 0.03%, about 0.04%, about 0.05%, about 0.06%, about 0.07%, about 0.08%, about 0.09%, 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, or about 3.0%. For example, the one or more preservatives and/or chelating agents may be present at about 0.5%, or about 0.2% by weight of the composition. The one or more preservatives and chelating agents may range from about 0.01% to about 3%, about 0.01% to about 2.5%, about 0.01% to about 2.0%, about 0.01% to about 1.5%, about 0.01% to about 1.0%, about 0.01% to about 0.8%, about 0.01% to about 0.6%, about 0.01% to about 0.4%, about 0.01% to about 0.2%, 0.1% to about 3%, about 0.1% to about 2.5%, about 0.1% to about 2.0%, about 0.1% to about 1.5%, about 0.1% to about 1.0%, about 0.1% to about 0.8%, about 0.10% to about 0.6%, about 0.10% to about 0.4%, about 0.10% to about 0.3%, about 0.10% to about 0.2%, about 0.2% to about 3%, about 0.2% to about 2.5%, about 0.2% to about 2.0%, about 0.2% to about 1.5%, about 0.2% to about 1.0%, about 0.2% to about 0.8%, about 0.2% to about 0.6%, about 0.2% to about 0.4%, about 0.2% to about 0.3%, about 0.3% to about 3%, about 0.3% to about 2.5%, about 0.3% to about 2.0%, about 0.3% to about 1.5%, about 0.3% to about 1.0%, about 0.3% to about 0.8%, about 0.3% to about 0.6%, about 0.3% to about 0.5%, about 0.4% to about 3%, about 0.4% to about 2.5%, about 0.4% to about 2.0%, about 0.4% to about 1.5%, about 0.4% to about 1.0%, about 0.4% to about 0.8%, about 0.4% to about 0.6%, about 0.6% to about 2.8%, about 0.6% to about 2.6%, about 0.8% to about 2.6%, about 0.8% to about 2.4%, about 0.8% to about 2.2%, about 0.8% to about 2.2%, about 0.8% to about 1.8%, about 0.8% to about 1.6%, about 0.8% to about 1.4%, about 0.8% to about 1.2%, about 1.0% to about 2.0%, about 1.0% to about 1.8%, about 1.0% to about 1.6%, about 1.0% to about 1.4%, about 1.0% to about 1.2%, about 1.2% to about 2.0%, about 1.2% to about 1.8%, about 1.2% to about 1.6%, about 1.2% to about 1.4%, about 1.4% to about 2.0%, about 1.4% to about 1.8%, about 1.4% to about 1.6%, about 1.6% to about 2.0%, or about 1.6 to about 1.8%. For example, the one or more preservatives and/or chelating agents may range from about 0.01% to about 3% by weight of the composition. In embodiments, the preservatives range from about 0.1% to about 1.5% by weight of the compositions and the chelating agents range from about 0.05% to about 0.5% by weight of the composition.

In embodiments, the preservatives are one or more preservatives selected from the group consisting of potassium sorbate, methyl paraben, and sodium benzoate.

In embodiments, the composition comprises one or more of: potassium sorbate, methyl paraben, sodium benzoate, pheoxyethanol, ethylhexylglycerin, pentylene glycol, and hydroxyacetophenenone.

In embodiments, the chelating agent is disodium EDTA.

In some embodiments, the formulation is free of preservatives.

In compositions of the present disclosure may also comprise one or more antioxidants.

The antioxidants may include ascorbic acid, cysteine, sodium bisulfate, sodium metabisulfite, sodium sulfite, ascorbyl palmitate, butylated hydroxyanisole (BHA), butylated hydroxytoluene (BHT), lecithin, propyl gallate, alpha-tocopherol (vitamin E), monothioglycerol, dithiothreitol and the like. For example, the antioxidant may be butylated hydroxyanisole (BHA).

The one or more antioxidants may range from about 0.005% to about 3%, about 0.005%, about 0.01% to about 2.5%, about 0.01% to about 2.0%, about 0.01% to about 1.5%, about 0.01% to about 1.0%, about 0.01% to about 0.8%, about 0.01% to about 0.6%, about 0.01% to about 0.4%, about 0.01% to about 0.2%, 0.1% to about 3%, about 0.1% to about 2.5%, about 0.1% to about 2.0%, about 0.1% to about 1.5%, about 0.1% to about 1.0%, about 0.1% to about 0.8%, about 0.1% to about 0.6%, about 0.1% to about 0.4%, about 0.1% to about 0.3%, about 0.1% to about 0.2%, about 0.2% to about 3%, about 0.2% to about 2.5%, about 0.2% to about 2.0%, about 0.2% to about 1.5%, about 0.2% to about 1.0%, about 0.2% to about 0.8%, about 0.2% to about 0.6%, about 0.2% to about 0.4%, about 0.2% to about 0.3%, about 0.3% to about 3%, about 0.3% to about 2.5%, about 0.3% to about 2.0%, about 0.3% to about 1.5%, about 0.3% to about 1.0%, about 0.3% to about 0.8%, about 0.3% to about 0.6%, about 0.3% to about 0.5%, about 0.4% to about 3%, about 0.4% to about 2.5%, about 0.4% to about 2.0%, about 0.4% to about 1.5%, about 0.4% to about 1.0%, about 0.4% to about 0.8%, about 0.4% to about 0.6%, about 0.6% to about 2.8%, about 0.6% to about 2.6%, about 0.8% to about 2.6%, about 0.8% to about 2.4%, about 0.8% to about 2.2%, about 0.8% to about 2.2%, about 0.8% to about 1.8%, about 0.8% to about 1.6%, about 0.8% to about 1.4%, about 0.8% to about 1.2%, about 1.0% to about 2.0%, about 1.0% to about 1.8%, about 1.0% to about 1.6%, about 1.0% to about 1.4%, about 1.0% to about 1.2%, about 1.2% to about 2.0%, about 1.2% to about 1.8%, about 1.2% to about 1.6%, about 1.2% to about 1.4%, about 1.4% to about 2.0%, about 1.4% to about 1.8%, about 1.4% to about 1.6%, about 1.6% to about 2.0%, or about 1.6 to about 1.8%. For example, the antioxidant may range from about 0.005% to about 0.5%, or about 0.01% to about 0.1% by weight of the composition.

In embodiments, the composition comprises a mucoadhesive polymer and clay particles and at least one or more additional components (e.g., 1 or 2 or 3 or 4 or 5 or 6 additional components) selected from: lipophilic excipients, viscosity modifiers, moisturizers, preservatives, chelating agents and buffering agents.

In embodiments, the composition comprises a mucoadhesive polymer and clay particles and at least one or more additional components (e.g., 1 or 2 or 3 or 4 or 5 or 6 additional components) selected from: lipophilic excipients, viscosity modifiers, moisturizers, antioxidants, chelating agents and buffering agents.

In some of these embodiments, the preservative-free formulation may be contained in a suitable device endowed with a liquid dispensing system capable of maintaining sterility of the solution before and upon multiple dosing for administration to various pathways including the nasal route. Dosing can be controlled through the use of a metered pump dispensing device, such as are known in the art. An example of such device is described in a Korean Patent No. KR101474858B1, incorporated by reference herein in its entirety. In some embodiments, the preservative-free composition is used in combination with a preservative-free dispensing system adequate to deliver the formulation to the nose, i.e., capable of functioning as a nasal spray. In some embodiments, such a combination product can be manufactured by aseptically filling the preservative-free sterilized formulation in sterilized bottles. A preservative-free spray pump system from Ursatec Verpackung GmbH is one such combination product where a built-in valve releases the nasal spray when the pump is depressed without allowing air to flow back into the bottle. The air passes through a special filter matrix that consists of an efficient material combination of filter, adsorption materials and silver. Another example of a combination product is a preservative-free pump system from Nemera where a mechanical closing tip avoids contamination through the orifice, while permeation through a silicone membrane allows for sterile air ingress. A yet another example of a preservative-free combination product is a nasal spray system from Aptar Pharma where a spring-loaded tip-seal mechanism prevents contamination, while a filter membrane in the ventilation channel ensures sterile air ingress.

A liquid composition and/or combination may also contain additives or excipients such as gluconic acid, lactic acid, citric acid or acetic acid, sodium gluconate, sodium lactate, sodium citrate, or sodium acetate. Selection of excipients and the amounts used may be readily determined by the formulation scientist based upon experience and consideration of standard procedures and reference works in the field.

The compositions and/or combinations of the invention may be in the form of an aqueous or oleaginous suspension. In some embodiments, the composition and/or combinations of the invention may be in the form of a sterile aqueous or oleaginous suspension. This suspension may be formulated according to the known art using suitable dispersing or wetting agents and suspending agents. The sterile solution or suspension may be dissolved or dispersed in a non-toxic pharmaceutically acceptable diluent or solvent, such as a solution in 1,3-butane-diol or prepared as a lyophilized powder for delivery as a dry powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides.

In some embodiments of the present disclosure, the composition can be formulated in any way suited for oral, nasal or a combination of oral and nasal administration.

In some embodiments, formulations of the present disclosure are in the form of in situ nasal gelling systems comprising stimulus responsive polymers. Stimulus responsive polymers include polymers that alter the rheological characteristics of in situ gelling formulations upon contact with the nasal mucosa due to changes in temperature, pH, or ions. Examples of stimulus responsive polymers or in situ gelling agents include, but are not limited to, poloxamers, pectin, and chitosan-based polymers. In some embodiments, in situ gelling systems may further comprise mucoadhesive excipients such as carbopol 934P, chitosan, sodium carboxymethyl cellulose (NaCMC), hydroxypropyl methylcellulose (HPMC), hydroxypropyl cellulose and methylcellulose. In some embodiments, nasal formulations comprising stimulus responsive polymers, which may optionally further comprise mucoadhesive excipients, e.g. those disclosed in Chonkar et al., *Indian J Pharm Sci.*, 2015 July-August; 77(4): 367-375, incorporated by reference herein in its entirety for all purposes.

In some embodiments, formulations comprising absorption enhancers such as alkyl glycosides disclosed in U.S. Pre-Grant Publication Nos. 2006/0045868, 2006/0045869, 2008/0299079 or formulations comprising soybean-derived stearyl glycoside and sterol mixtures as absorption enhancers (Ando et al., Biological and Pharmaceutical Bulletin, 21(8), 862-865) may be used to provide sustained release, each of these documents is herein incorporated by reference for all purposes. In some embodiments, formulations comprising micelles of sodium glycocholate or micelles of sodium glycocholate mixed with fatty acid (e.g. linoleic acid) as absorption enhancers may be used as sustained release formulations. Other examples of absorption enhancers include cyclodextrins, phospholipids, and chitosans.

Exemplary nasal formulations based on thermogelling polymers such as poloxamers are disclosed by Sharma et al. (Drug Dev Ind Pharm. 2014 July; 40(7):869-78); Cho et al. (J Pharm Sci. 2011 February; 100(2):681-91); Choi et al. (Int Forum Allergy Rhinol. 2017 July; 7(7):705-711); and Balakrishnan et al. (Molecules. 2015 Mar. 4; 20(3):4124-35), each of these documents is incorporated by reference herein in its entirety for all purposes.

In some embodiments, the composition of the present disclosure is administered nasally or orally in drops, spray, gel, ointment, cream, or suspension. In some embodiments, the composition of the present disclosure is administered nasally using a dispenser or a device (for example a single-dose ampoule, metered spray, an atomizer, a nebulizer, a pump, a nasal pad, or a nasal sponge) or any other method of nasal administration which is known in the pharmaceutical literature.

In some embodiments, devices for nasal administration of liquid compositions of the present disclosure include a pipette (e.g. unit dose pipettes); a dropper including multi-dose droppers; rhinyle catheter; a vapor inhaler; mechanical spray pumps, including squeeze bottles, multi-dose metered-dose spray pumps, single or duo-dose spray pumps, bi-directional multi-dose spray pumps; gas driven spray systems/atomizers and electrically powered nebulizers/atomizers. These devices are briefly summarized in a review by Djupesland (Drug Deliv. and Transl. Res. (2013) 3:42-62), which is incorporated by reference herein in its entirety.

In some embodiments, the composition of the present disclosure is administered to the nasal cavity in metered doses. In some embodiments, a metered dose nasal spray can be used to administer the composition of the present disclosure. In some embodiments, a metered nasal pump spray can be used to administer the composition of the present disclosure in metered doses. In some embodiments, a metered atomizing spray pump can be used to administer the composition of the present disclosure in metered doses.

In some embodiments, a nasal pressurized metered-dose inhaler (pMDI) can be used to administer the composition of the present disclosure in metered doses. In some embodiments, pressurized nasal formulation of the present disclosure can be an aerosol formulation. Such aerosol formulation, in some embodiments, includes the composition in a pressurized pack with a suitable propellant such as a hydrofluoroalkanes (HFAs), carbon dioxide, or other suitable propellant known in the art. The aerosol can, in some embodiments, also contain a surfactant such as lecithin.

In some embodiments, the composition of the present disclosure is administered to the nasal or oral cavity by conventional means, e.g., with a dropper, pipette, spray, pump spray, breath-actuated pMDI, RetroNose device, or throat spray pump.

In some embodiments, the compositions of the present disclosure are administered 1, 2, 3, 4, 5, 6, 7 8, 9, or 10 times a day. In some embodiments, the compositions of the present disclosure are administered one or more times a day, where each dose administers a controlled, metered, or set amount of the composition.

In some embodiments, the intranasal compositions of the present disclosure are administered 1, 2, 3, 4, 5, 6, 7 8, 9, or 10 times a day. In some embodiments, the intranasal compositions of the present disclosure are administered once a day, twice a day, three times a day, four times a day, five times a day, or six times a day where each dose administers a controlled, metered, or set amount of the composition. In some embodiments, the intranasal composition of the present disclosure is administered three times a day. In some embodiments, the intranasal compositions of the present disclosure are administered up to six times a day.

In some embodiments, a composition of the present disclosure is a solution, suspension, or aerosol. In some embodiments, the composition of the present disclosure is an aqueous solution.

All publications and patents mentioned herein are hereby incorporated by reference in their entirety as if each individual publication or patent was specifically and individually indicated to be incorporated by reference. In case of conflict, the present application, including any definitions herein, will control.

While specific embodiments of the subject disclosure have been discussed, the above specification is illustrative and not restrictive. Many variations of the disclosure will become apparent to those skilled in the art upon review of this specification and the claims below. The full scope of the disclosure should be determined by reference to the claims, along with their full scope of equivalents, and the specification, along with such variations.

EXAMPLES

Example 1: In Vitro Analysis of SARS-CoV-2 Binding by Bentonite Suspensions

Objective: Assess if bentonite suspended in water could bind SARS-CoV-2 virus, thus lowering the virus's ability to infect cells.

The following test items were used: Vicks First Defence, a composition trapping and neutralizing the viruses which cause cold and flu symptoms which is marketed in spray form (HPMC, succinic acid, disodium succinate, PCA, phenethylalcohol, zinc EDTA, zinc acetate, polysorbate 80, aroma: (menthol, camphor, eucalyptol), sodium saccharin); and Veegum HS (purified bentonite NF). Samples of Vicks were diluted 10-fold in water. Water was added to Veegum Bentonite to achieve aqueous solutions having 0.04%, 0.08%, and 0.16% by weight bentonite.

Procedure: 100 µl of SARS-CoV2 ($10^{\wedge}6$ infectious units) were added to 900 ul of each bentonite suspension as well as the non-bentonite sample (Vicks) and each sample was incubated for 5, 15, and 45 minutes at 32° C. A gel separation column (Sephadex microspin column) was used to separate off the bentonite from the solution which contained unbound virus. Each sample was then serially diluted and incubated with a Vero cell line and the viral titer was measured at day 6 to determine the cytopathological effect by measuring the TCID50 (Median Tissue Culture Infectious Dose).

Results: FIG. 1 shows the reduction of viral infectious load after bentonite incubation after 5, 15, and 45 minutes. After 5 minutes of incubation, all bentonite-containing solutions achieved a viral infectious load reduction of greater than 90%, with two of the bentonite solutions (0.04% and 0.16% bentonite) achieving close to 99% viral infectious load reduction. Similarly, at 15 minutes and 45 minutes of incubation, all of the bentonite-containing solutions achieved close to a 99% viral infectious load reduction. In contrast, the non-bentonite containing solution (Vicks) showed a negative viral infectious load reduction at each tested incubation time-point.

Conclusion: It was believed that SARS-Cov-2 particles would adsorb to and/or bind to bentonite-containing solutions, thereby inactivating the pathogen. The results described in this example confirm this hypothesis, showing that even after 5 minutes of incubation, all bentonite-containing solutions achieved a viral infectious load reduction of greater than 90%, with most solutions achieving close to 99% viral infectious load reduction. Non-bentonite solutions displayed no viral infectious load reduction, which further confirmed this hypothesis.

Example 2—Development and Preparation of Thixotropic Formulations

Objective: To formulate bentonite compositions suitable for intranasal delivery, with good local tolerability and safety and extended nasal residence time compared to traditional aqueous solution nasal sprays.

In order to maximize nasal residence time for extended protection, development of a thixotropic formulation was sought, i.e. a formulation that is a viscous gel which upon shaking in the spray device moves to sol state for spraying and reverts back to gel state upon deposition on the nasal mucosa.

Materials and methods: A design space was defined based on combinations of several key components: bentonite (Veegum K), viscosity modifiers (xanthan gum, glyceryl stearate, caprylic/capric triglyceride), humectants (glycerol), and buffers (citric acid), yielding a total of 63 formulations. Components and maximum concentrations were selected based on available safety and tolerability data as well as regulatory status (FDA list of inactive ingredients, generally recognized as safe, GRAS).

Feasibility and suitability of the formulations were evaluated based on a number of factors, including manufacturing feasibility (solubilization of raw materials and homogeneity after high shear mixing), texture, adherence to surface and tackiness, rheology (G* complex modulus, G' storage modulus by sweep amplitude testing; thixotropy by ORO test examining G' regeneration [%] up to 240" and shear viscosity curves), and—for the lead candidates—also sprayability with a nasal spray pump (plume geometry, spray pattern, manual evaluation of actuation force). Rheology measures were performed on an MCR 102 Antoon Paar rheometer.

Results: From the formulation development work, two lead formulations emerged, shown below:

TABLE 1

Formulation 60 (F060) - gel emulsion (oil in water gel)

| Component | % (w/w) | Function |
| --- | --- | --- |
| Purified water | QS 100 | Solvent |
| Caprylic/capric triglyceride (Miglyol 812N) | 35.00 | Viscosity modifier, emulsifying agent |
| Bentonite (VEEGUM® K Bentonite) | 2.50 | Rheological modifier and barrier constituting agent |
| Glycerol | 2.50 | Humectant |
| Glyceryl stearate (Geleol mono and Diglycerides) | 1.50 | Viscosity modifier, thickener |
| Xanthan gum (XANTURAL 180) | 0.20 | Viscosity modifier, thickener |
| Potassium sorbate | 0.12 | Preservative |
| 1M Citric acid to pH 5 | 0.46 | Buffering agent |
| Methyl paraben (Methyl-4-hydoxy-benzoate) | 0.10 | Preservative |
| Disodium EDTA (Sodium edetate TITRIPLEX III)) | 0.02 | Chelating Agent |

Formulation 60 was prepared as follows:

Mix 1: Methyl paraben was dissolved at 75° C. in water by stirring until complete dissolution. Veegum K and Xanthan gum were added to the water while stirring with a high shear mixer at 12000 rpm for 15 minutes at 75±1° C.

Mix 2: Glycerol, Miglyol 812 N and Geleol were heated and mixed to 70±1° C.

Mix 3: Potassium sorbate and disodium EDTA were solubilized in water.

Step 1: Mix 2 was added to mix 1 while mixing at 10000 rpm for 5 minutes at 75° C.

Step 2: After the gel emulsion from Step 1 was left to cool down at <35° C., mix 3 was added after mixing at 10000 rpm for 5 minutes.

Step 3: pH was adjusted with 1M citric acid to pH 5.0 and homogenized for 5 minutes at 10000 rpm.

Step 4: The preparation was brought to final volume with water and homogenized for 5 minutes at 10000 rpm.

TABLE 2

Formulation 049 (F049) - aqueous solution

| Component | % (w/w) | Function |
| --- | --- | --- |
| Purified water | QS 100 | Solvent |
| Bentonite (VEEGUM® K Bentonite) | 3.00 | Rheological modifier and barrier constituting agent |
| Glycerol | 2.50 | Humectant |
| Glyceryl stearate (Geleol mono and Diglycerides) | 1.50 | Viscosity modifier, thickener |
| Xanthan gum (XANTURAL 180) | 0.40 | Viscosity modifier, thickener |
| Potassium sorbate | 0.12 | Preservative |
| 1M Citric acid to pH 5 | 0.40 | Buffering agent |
| Methyl paraben (Methyl-4-hydoxy-benzoate) | 0.10 | Preservative |
| Disodium EDTA (Sodium edetate TITRIPLEX III)) | 0.02 | Chelating Agent |

Formulation 49 was prepared as follows:

Mix 1: Methyl paraben was dissolved at 75° C. in water by stirring until complete dissolution. Veegum K and Xanthan gum were added to the water while stirring with high shear mixer at 12000 rpm for 15 minutes at 75±1° C.

Mix 2: Potassium sorbate, glycerol and disodium EDTA were solubilized in water.

Step 1: Mix 1 was left to cool down at <35° C., mix 2 was added after mixing at 10000 rpm for 5 minutes.

Step 2: pH was adjusted with 1M citric acid to pH 5.0 and homogenized for 5 minutes at 10000 rpm.

Step 3: The preparation was brought to final volume with water and homogenized for 5 minutes at 10000 rpm.

Conclusions: The experiment resulted in two lead formulations with desired characteristics and properties, namely components with good safety and tolerability, structure in the gel stage (acceptable G' and G*, respectively storage and complex modulus), sprayability with a standard commercial nasal spray pump after shaking, restoration of structure after spraying and contact with mucosal surface in a short time (acceptable G' storage modulus restoration 240" after shear stress), and acceptable spray characteristics (homogeneous spray pattern, ease of actuation, acceptable spray plume).

Example 3—Protective Effects in Human Airway Epithelium Cell Assay

Objective: To assess the capability of gel formulations comprising bentonite to prevent or mitigate SARS-CoV-2 infection of nasal epithelium cells.

Materials and methods: For the experiment, reconstituted human nasal epithelia (MucilAir™, Epithelix) from 14 healthy donors were used. These epithelial cultures morphologically and functionally resemble the upper conducting airways, they produce mucus and exhibit active ciliary-beating and mucociliary clearance much like in vivo epithelium. As such they provide a universal platform to study the effects of human respiratory viruses.

The nasal epithelial cell cultures were prepared in 0.7 mL medium and stored at 37° C. during routine culture and at 34° C. during testing. Prior to treatment and infection of inserts, the apical side was gently washed to remove mucus (200 μL discarded). Then 10 μL of the following test items (diluted 1:5) were added to the apical side: F060 and F49 (two bentonite formulations disclosed in Example 2), or their vehicles F060(-) and F49(-). For comparison, dissolved hydroxypropylmethylcellulose (Nasaleze 5 mg/mL), a nasal powder used as barrier against viruses or allergens, was added. Saline solution added to infected cultures served as main control, untreated, non-infected cells as culture control. Non-infected cells treated with F060 served as additional control. Following treatment, 100 μL SARS-CoV-2 suspension was added at a multiplicity of infection of 0.5 ($2.5 \times 10^6$ $TCID_{50}$; Texcell). Three hours later the apical side was gently washed 3× with 200 μL culture medium to remove unbound virus; then 300 μL culture medium was added on the apical side and removed 20 minutes later for viral quantification ($TCID_{50}$). Next, the inserts were transferred into a new culture plate containing 500 μL medium, a sample from the basal-lateral side was taken, and 10 μL of the test item was added. The cell culture was then incubated for 21 hours.

After 24, 48, 72 and 96 hours each, a 300 μL culture medium was added on the apical side and removed 20 minutes later for viral quantification, the inserts were transferred into a new culture plate containing 500 μL medium, a sample from the basal-lateral side was taken, and 10 μL of the test item was added (except after 96 hours). In case of one separate cell culture treated with F060, no apical washing was performed, allowing the virus to accumulate for 4 days while 10 μL of test item F060 was added every 24 hours (last addition at 72 hours).

Each sample was then serially diluted and incubated with a Vero cell line, and the viral titer was measured at day 6 with crystal violet stain to determine the cytopathological effect ($TCID_{50}$).

Results: In saline-treated nasal epithelium, Sars-CoV-2 replicated efficiently. As shown in FIG. 2, clear virus growth could be observed 48 h after infection and virus titers increased over 96 h to a mean of $6.9 \times 10^6$ $TCID_{50}$/mL. In comparison, in nasal epithelium treated with the bentonite composition F060, mean virus titers with apical washing were 90.0% lower at 48 h ($p<0.05$) and 99.2 and 99.4% lower at 72 and 96 h, respectively ($p<0.001$). Without apical washing, mean virus titers were 92.4% lower at 96 h ($p<0.001$). Treatment with bentonite composition F049 resulted in reduced viral titers as well, however, the reduction became apparent later and was smaller than with F060 (61.1% at 72 h and 71.8% at 96 h; not significant). The vehicles F060(-) and F049(-) appeared to have no effect on viral growth and viral titers. Treatment with IPMC showed no significant effect, either. The culture control as well as the non-infected culture treated with F060 appeared inconspicuous.

Conclusions: Repeated treatment with bentonite compositions is effective in significantly mitigating Sars-CoV-2 infection of nasal epithelial cells. As the vehicles of the tested compositions per se did not show protective effects, the inhibitory effect is exerted by the bentonite ingredient. Surprisingly, a synergistic effect between the formulation and bentonite was observed in the case of F060 which contained less bentonite than F049 (2.5 vs. 3.0%), but showed more pronounced effects. Unlike F049, which is an aqueous formulation, F060 is a gel emulsion (oil in water). Without being bound by theory, this increased efficacy may be related to the fact that bentonite acts as an emulsion stabilizer, positioning itself at the interface between the oil droplets and the aqueous phase. Another hypothesis is that the bentonite at the interface of the oil in water phase, recruiting the virus particles in intimate proximity of the oil droplet, may enhance the entrapment of the viral particle within the oil droplet Example 4—Development and Preparation of Formulations for Use in Protection Against Airborne Viruses, Allergens and Other Particles Objective: To develop a product comprising a thixotropic formulation including bentonite that can be administered via a common nasal spray device designed to have little-to-no preservative. The product should be easy to administer, well tolerated in the nose and throat, comply with relevant regulatory requirements and be suitable for manufacturing in large volumes.

Materials and methods: Starting from composition F060 disclosed in Example 2, various variants were evaluated based on several factors. These included manufacturing feasibility (solubilization of raw materials and homogeneity after high shear mixing), texture, adherence to surface and tackiness, rheology (G* complex modulus, G' storage modulus by sweep amplitude testing; thixotropy by ORO test examining G' regeneration [%] up to 240" and shear viscosity curves), proper dispensing capabilities at industrial scale and according to current pharmaceutical standards, acceptable physical and chemical stability during manufacturing process, storage and in-use.

Further, the assessment included compatibility with nasal spray devices, consistent spray characteristics after simple shaking (homogeneous spray pattern, ease of actuation, acceptable spray plume, plume geometry, droplet size distribution, absence of residual drop on the tip of the nasal spray), manual evaluation of actuation force, easiness of priming and compatibility with bottles. Further, testing also included user assessments of smell and taste, tolerability and handling. Lastly, aspects of user friendliness for long term and frequent daily use were considered, including absence of preservatives, thorough compatibility with the nasal mucosa and nasal symptoms.

Results: The development work resulted in a preservative-free gel emulsion (6PF3), filled into 20 mL HDPE bottles (ref P-3696, Röchling, Mannheim) connected to a nasal spray pump (APF, Aptar, Radolfzell) which delivers approximately 120 sprays of about 140 µL each.

TABLE 3

Formulation 6PF3 - gel emulsion (oil in water gel)

| Component | % (w/w) | Function |
| --- | --- | --- |
| Purified water | QS 100 | Solvent |
| Caprylic/capric triglyceride (Miglyol 812N) | 35.00 | Viscosity modifier, emulsifying agent |
| Bentonite (VEEGUM ® K Bentonite) | 2.50 | Rheological modifier and barrier constituting agent |
| Propylene glycol | 5.0 | Humectant |
| Glyceryl stearate (Geleol mono and Diglycerides) | 1.50 | Viscosity modifier, thickener |
| Xanthan gum (XANTURAL 180) | 0.20 | Viscosity modifier, thickener |
| Mannitol | 0.12 | Humectant |
| BHA (Butylated hydroxyanisole) | 0.02 | Antioxidant |
| Disodium EDTA (Sodium edetate TITRIPLEX III)) | 0.2 | Chelating Agent |
| Citric acid | To pH 5.0 | Buffering agent |

Formulation 6PF3 was prepared as follows:

Aqueous phase: water was heated to 70° C.+/−5° C., sodium EDTA was added and completely dissolved for e.g. 5 minutes. Mannitol was added and dissolved for about 5 minutes. Propylene glycol was added and dissolved for about 10 minutes. Xanthan Gum and Veegum K were added and homogenized for e.g. 25 minutes at about 3000 rpm.

Oily phase: Miglyol 812N and Geleol Mono and Diglycerides were mixed and heated to 70° C.+/−5° C. BHA was added and homogenized for about 5 minutes.

The oily phase was added to the aqueous phase and emulsified at 70° C. for about 35 minutes at about 3000 rpm.

Cooling was performed while mixing and homogenizing until temperature was <35° C. PH adjustment was performed adding a concentrated solution of citric acid until pH 5.0 was reached while homogenizing. The preparation was brought to final volume with water and homogenized for about 5 minutes at about 1500 rpm.

The preparation was filled into the 20 mL bottles, which were closed with the nasal spray pump.

Microbial decontamination strategies such as autoclaving or gamma irradiation were tested on the bulk product and the finished product.

Conclusions: The experiment resulted in a suitable combination product comprising a physically stable formulation and a spray pump with desired characteristics and properties, namely sprayability with consistent and acceptable spray characteristics (homogeneous spray pattern, ease of actuation, acceptable spray plume). The ingredients of the formulation have excellent safety and tolerability, appropriate structure in the gel stage (acceptable G' and G*, respectively storage and complex modulus) to allow for long residence time in the nasal cavity, restoration of structure after spraying and contact with mucosal surface in a short time (acceptable G' storage modulus restoration 240" after shear stress).

Example 5—Testing Barrier Function Against Allergens in Diffusion Barrier Assay

Objective: To assess the capacity of gel formulations comprising bentonite to act as barrier to prevent diffusion of allergen particles towards the nasal epithelium.

Materials and methods: For the experiment agar blocks were used to simulate the nasal mucosa as described previously (Diethart B, Emberlin J C, Lewis R A. Hydroxypropylmethylcellulose gel application delays Der p 1 diffusion in vitro. Natural Sci. 2010; 2(2):79-84, incorporated herein by reference in its entirety for all purposes). Ten mL of agar (1.5%, Agar-agar ultrapure, Merck, Darmstadt; prepared with 0.9% saline solution) were cast into a 10 cm petri dish. After cooling, small rectangles (1×1 cm) were cut from the agar and transferred to cleaned glass slides. Small lines of warm and therefore liquid Vaseline were drawn from the two edges of one side of the agar block to the edges of the slides to prevent diffusion of the test item through the side of the block. The agar block was covered by a cover slip that sealed the upper surface of the agar. Therefore, diffusion into the agar was possible only through one free edge.

The test item was the gel 6PF3 as described in Example 4. It was applied with sterile 1 mL syringes in a total volume of 40 µL to the open side of the agar block, resulting in an initial thickness of 3-4 mm. After covering with a cover slip, 20 µL of an allergen solution (recombinant Timothy grass pollen allergen Phi p 5a at 6000 ng/mL; Indoor Biotechnologies, Charlottesville) were applied onto the test item or directly on the agar block (negative control). In one additional control group, 40 µL of agar were applied instead of the test item (agar control). The slides were incubated at 35° C. and 90% relative humidity to simulate nasal conditions for 15, 30, 60, 180 and 360 minutes. All tests were performed in quadruplicates, except for the agar control (in triplicate).

The agar blocks were then carefully removed from the slides and transferred to labelled sterile microtubes containing 0.5 mL of an elution medium (phosphate buffer saline with 0.05% v/v Tween20). Samples were vortexed for 20 seconds and shaken overnight at room temperature. The samples were collected from the tubes and stored at −80° C. until measurement with ELISA (Antibody kit PhI p 5, Indoor Biotechnologies, Charlottesville).

Results: In the negative control group, allergen recovery increased over time to 70.5% after 6 hours. In the agar control group, recovery was 46.0% (only performed after 6 hours). Application of the test item resulted in no detectable allergens at all time points except one (12.8% after 1 hour).

Conclusions: Application of a bentonite composition is effective at preventing diffusion of allergen particles to the nasal epithelium by establishing a physical barrier that is impermeable or difficult to permeate. Under ambient conditions simulating those inside the nasal cavity, the barrier effect is lasting for several hours.

Example 6—Clinical Evaluation of Protection Against Airborne Allergens

Objective: to compare the clinical performance and safety of a nasal spray comprising a thixotropic bentonite composition (AM-301) against hydroxypropylmethylcellulose (HPMC) powder in alleviating the symptoms of allergic rhinitis triggered by grass pollen exposure in an allergen challenge chamber (ACC). In a placebo controlled study conducted during grass pollen allergy season, the IPMC treated group had been shown to require significantly lower amounts of rescue medication (e.g. antihistamines, nasal sprays and eye drops) than the placebo group (Emberlin, J., & Lewis, R. (2006). A double blind, placebo controlled trial of inert cellulose powder for the relief of symptoms of hay fever in adults. *Current Medical Research and Opinion*, 22(2), 275-285, incorporated herein by reference in its entirety for all purposes.

Materials and methods: The experiment was conducted as an open-label, cross-over, randomized, monocentric clinical investigation in a validated ACC environment. The use of an ACC allows exposure to a controlled amount of allergen, hence eliminating the confounding effect of environmental factors, mainly of variations in pollen exposure in seasonal disease. 36 patients with a history of allergic rhinitis to grass pollen participated in three ACC sessions, each of 4 hours duration. Within the ACC, they were exposed in the ACC to *Dactylis glomerata* pollen (4000±800 grains per $m^3$; Pharmallerga, Lisov, Czech Republic). Study participants recorded every 20 minutes their Total Nasal Symptom Score (TNSS). The TNSS is defined as the sum of nasal symptoms of obstruction, rhinorrhea, itching and sneezing, each of which is scored on a scale from 0 to 3.

During the first ACC session, eligibility for study inclusion was determined, which included a TNSS score of 6 or greater at least two times during the allergen challenge. After the screening phase, participants were randomized to receive either AM-301 or HPMC (Nasaleze, Isle of Man, UK) in a single dose (one puff per nostril) 10 minutes prior to their second ACC session. The composition of AM-301 is shown below in Table 4.

TABLE 4

Formulation AM301

| Component | % (w/w) | Function |
| --- | --- | --- |
| Purified water | QS 100 | Solvent |
| Caprylic/capric triglyceride (Miglyol 812N) | 35.0 | Viscosity modifier, emulsifying agent |
| Bentonite (VEEGUM ® K Bentonite) | 2.5 | Rheological modifier and barrier constituting agent |
| Propylene glycol | 5.0 | Humectant |
| Glyceryl stearate (Geleol mono and Diglycerides) | 1.5 | Viscosity modifier, thickener |
| Xanthan gum (XANTURAL 180) | 0.2 | Viscosity modifier, thickener |
| Potassium Sorbate | 0.6 | Preservative |
| Methyl paraben (Methyl-4-hydoxy-benzoate) | 0.2 | Preservative |
| Sodium Benzoate | 0.5 | Preservative |
| Disodium EDTA (Sodium edetate TITRIPLEX III)) | 0.2 | Chelating Agent |
| Citric acid | To pH 4.9 | Buffering agent |

For the third ACC session, which took place at least one week after the second session, the treatment was alternated. The difference in the TNSS average over the 4-hour pollen exposure between AM-301 and HPMC was the primary efficacy endpoint; further analyses included also the reduction in the TNSS from the unprotected exposure during the first ACC session to the protected exposure during the following ACC sessions as well as the safety and tolerability of the treatments.

Figure 3:
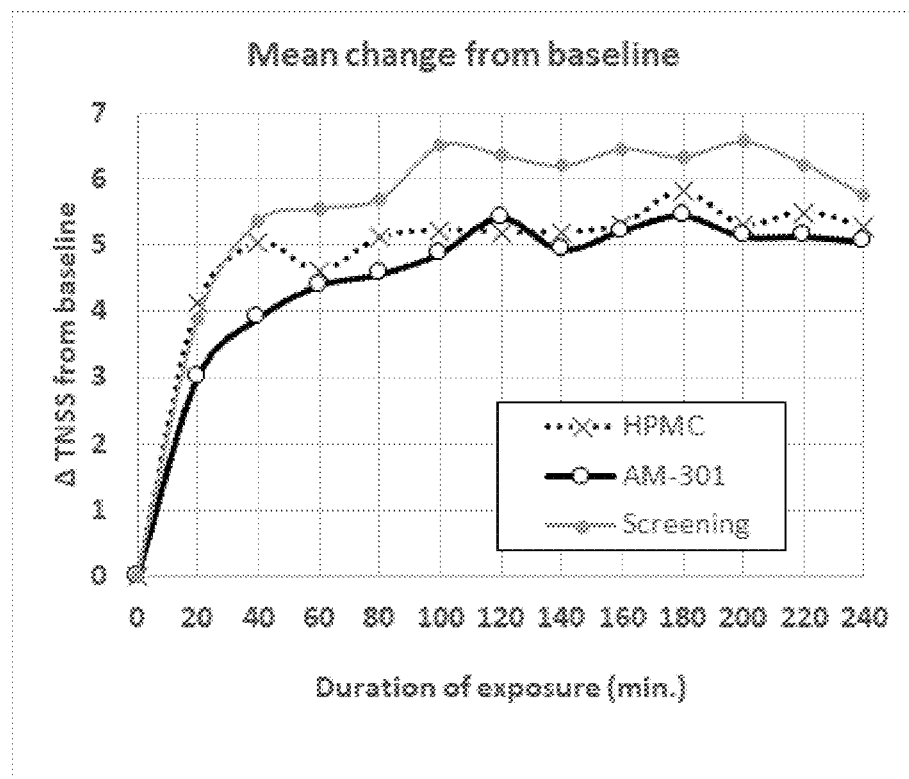
FIG. 3 shows comparative results of AM-301 and hydroxypropylmethylcellulose (HPMC) powder in alleviating the symptoms of allergic rhinitis triggered by grass pollen exposure in an allergen challenge chamber (ACC).

Results: Treatment with AM-301 yielded lower TNSS values than treatment with HPMC, especially during the first 40 minutes of pollen exposure (FIG. 3). For the remainder of the exposure, TNSS values largely converged. On average, treatment with AM-301 resulted in a reduction of the TNSS of about 1.1 points vs. the unprotected exposure, which exceeded the reduction observed with IPMC (0.7 points). Treatment with AM-301 provided protection for at least three hours and was well tolerated by participants.

Conclusions: Single dose administration of a composition comprising bentonite with a nasal spray prior to pollen exposure reduces the symptoms of allergic rhinitis. The protective effect sets in rapidly and lasts for at least three hours.

Example 7: Protective Effects with Treatment Starting Only after Viral Infection Onset Objectives: To assess the capability of gel formulations comprising bentonite to mitigate established SARS-CoV-2 infections 24 or 30 hours from infection of human nasal mucosal epithelia. The experiment was performed to complement the results from Example 3 which had demonstrated effective reduction of viral titers when treatment with a gel formulation comprising bentonite started concurrently with SARS-CoV-2 infection.

Materials and methods: For the experiment, the same assay as described in Example 3 was employed. The gel formulation 6PF3 described in Example 4 served as test item; its vehicle as well as saline solution served as controls.

Nasal epithelia cultured on inserts were infected with SARS-CoV-2. After 24 hours and 30 hours, formulation 6PF3 (or control) was applied on infected inserts. The apical medium from these inserts was collected at defined time points and tested for TCID50 on a VERO cell line.

For the epithelia treated 24 hours after infection, medium was applied on the apical side, collected 20 minutes later and 10 μL of the test item was added (except after 96 hours) as for Example 3 at the following time points: 24 hours (right before addition of 6PF3), 48, 72 and 96 hours.

For epithelia treated 30 hours after infection, medium was applied on the apical side, collected 20 minutes later and 10 μL of the test item was added (except after 96 hours) as for Example 3 at the following time points: 30 hours (right before addition of 6PF3), 54, 78 and 102 hours.

Similarly as for Example 3, in one condition for each time-course ("no wash"), no apical washing was performed, allowing the virus to accumulate for 4 days while 10 μL of 6PF3 was added every 24 hours (last addition at the next to last time point).

Figure 4:
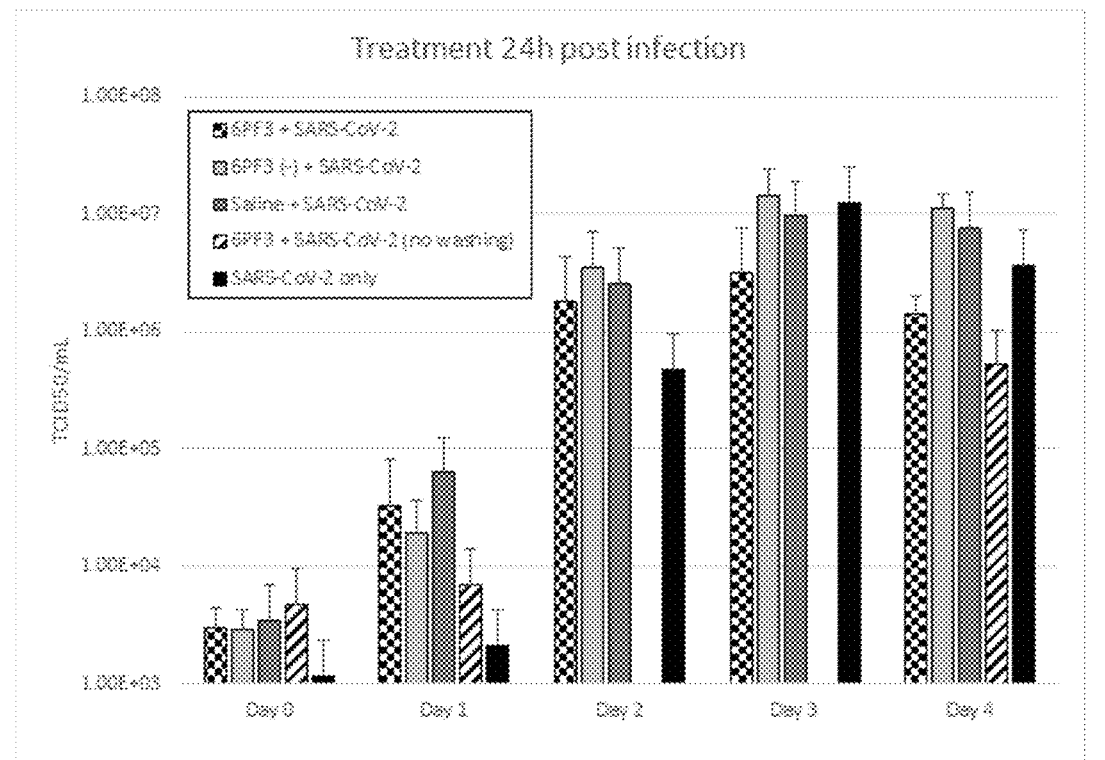
FIG. 4 shows the capability of gel formulations comprising bentonite to mitigate established SARS-CoV-2 infections 24 hours (top) or 30 hours (top) from infection of human nasal mucosal epithelia.
Figure 4:
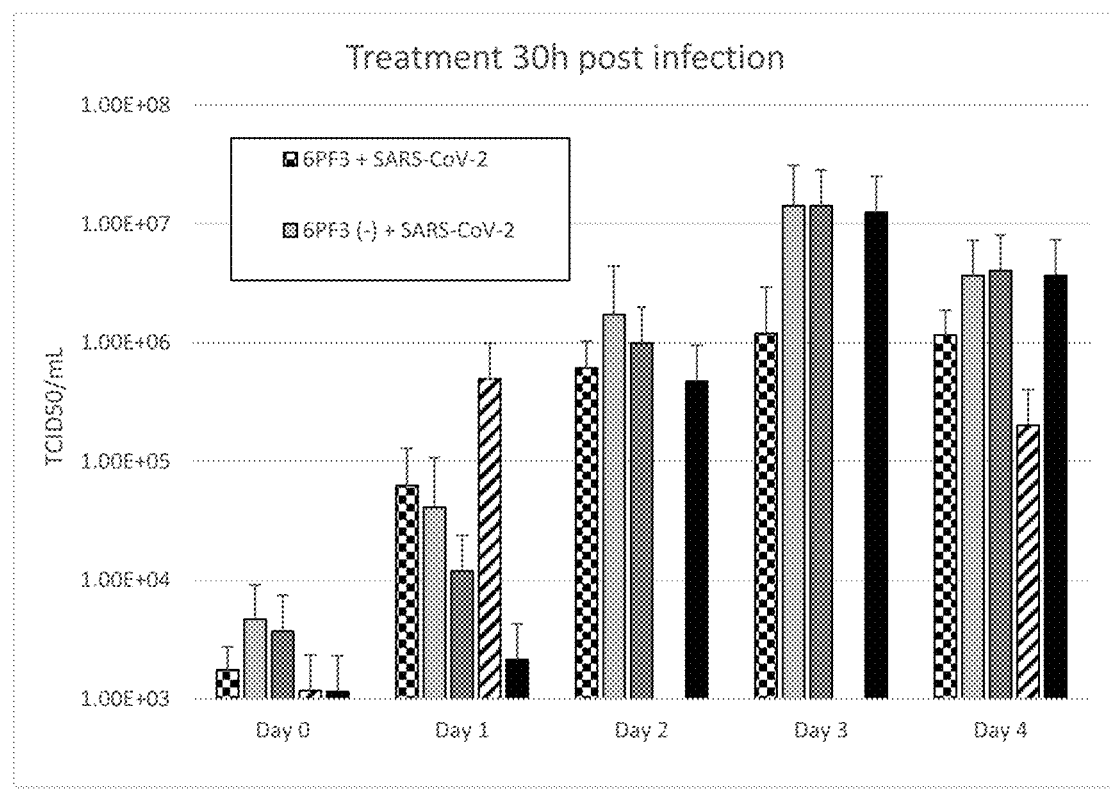

Results: as in Example 3, in each infected nasal epithelium that was treated with vehicle or saline or left non-treated, SARS-CoV-2 replicated efficiently (FIG. 4). Clear virus growth could be observed especially from 48 hours after infection. Average TCID50 values at Day 3 were $1.22 \times 10^7$ TCID50/mL for all conditions combined except 6PF3 and $7.59 \times 10^6$ TCID50/mL at Day 4. In comparison, for the treatment schedule started 24 hours post-infection: (i) epithelia treated with 6PF3 and washed every 24 hours showed $3.23 \times 10^6$ TCID50/mL at Day 3 and $1.42 \times 10^6$ TCID50/mL at Day 4, corresponding to approximately 3.5 and 10 times lower SARS-CoV-2 infectious load, respectively; (ii) epithelia treated with 6PF3 and not washed showed $7.84 \times 10^5$ TCID50/mL at Day 4, corresponding to about 18 times lower SARS-CoV-2 infectious load.

For the treatment schedule started 30 hours post-infection: (i) epithelia treated with 6PF3 and washed every 24 hours showed $1.19 \times 10^6$ TCID50/mL at Day 3 and $1.16 \times 10^6$ TCID50/mL at Day 4, corresponding to approximately 12.3 and 3.8 times lower SARS-CoV-2 infectious load; (ii) epithelia treated with 6PF3 and not washed showed 2.37×10$^5$ TCID50/mL at Day 4, corresponding to about 18 times lower SARS-CoV-2 infectious load.

Conclusions: Repeated treatment with bentonite compositions is effective in significantly mitigating established SARS-CoV-2 infection of and viral load on human nasal mucosal epithelia even when treatment is initiated only 24 hours and 30 hours post-infection.

Example 8: Protective Effects in Influenza a (H1N1) Infection

Objectives: To assess the capability of gel formulations comprising bentonite to help prevent or mitigate infection of human nasal mucosal epithelia by influenza A virus of the H1N1 subtype. The experiment was performed to complement the data obtained with SARS-CoV-2 and demonstrate that the invention does provide protection against infection by other types of virus as well. Well-known outbreaks of H1N1-type influenza A in humans include the 2009 swine flu pandemic.

Materials and methods: For the experiment, the same assay as described in Example 3 was employed. The gel formulation 6PF3 described in Example 4 served as test item; its vehicle as well as saline solution served as controls.

Nasal epithelia cultured on inserts were inoculated with H1N1 (LSS3; MOI=0.2) either 10 minutes after the first application of 6PF3 (to test the formulation's preventive effects) or 24 hours prior to the first application of 6PF3 (to test the formulation's mitigative effects). Similarly as for Examples 3 and 7, the 6PF3 formulation was applied daily for four days. Medium was applied on the apical side, collected 20 minutes later and 10 μL of the test item was added (except after 96 hours) as for Examples 3 and 7 at the following time points: 24, 48, 72 and 96 hours. The apical medium from the inserts was tested for TCID50 on a MDCK cell line. All tests were performed on 6 inserts each.

Results: Clear virus growth could be observed in saline- or vehicle treated epithelia especially from 48 hours after infection. In the prophylaxis experiment (treatment started 10 minutes prior to inoculation), average TCID50 values at Day 3 were 11×10$^6$ TCID50/mL for both controls and 4.0 and 2.9×10$^6$ TCID50/mL, respectively at Day 4. In contrast, epithelia treated with 6PF3 showed values of 0.94 and 0.65×10$^6$ TCID50/mL at Days 3 and 4, respectively, representing reductions in viral load of 84% and 85% vs. saline control. A Mixed-Effect Model Repeated Measure (MMRM) model with log-transformed TCID50 values showed for the comparison of the 6PF3 group with saline control a ratio of generalized least square means (GLSmeans) of 0.03 ($p=0.0128$) for Day 3 and 0.04 ($p=0.0056$) for Day 4. For the comparison of the 6PF3 group with vehicle control, the GLSmeans ratios were 0.12 ($p=0.0178$) and 0.25 ($p=0.0533$), respectively.

In the mitigation experiment (treatment started 24 hours after inoculation), average TCID50 values at Day 3 were 3.3 and 2.9×10$^7$ TCID50/mL for saline and vehicle controls, respectively, and 2.1 and 1.7×10$^7$ TCID50/mL, respectively at Day 4. In contrast, epithelia treated with 6PF3 showed values of 4.5 and 4.7×10$^6$ TCID50/mL at Days 3 and 4, respectively, representing reductions in viral load of 86% and 77% vs. saline control. The MMRM model with log-transformed TCID50 values showed for the comparison of the 6PF3 group with saline control a GLSmeans ratio of 0.13 ($p=0.0050$) for Day 3 and 0.23 ($p=0.0033$) for Day 4. For the comparison of the 6PF3 group with vehicle control, the GLSmeans ratios were 0.15 ($p=0.0073$) and 0.25 ($p=0.0051$), respectively.

Conclusions: Repeated treatment with bentonite compositions is effective in helping to prevent influenza A (H1N1) infection when applied to the nasal epithelium by reducing the viral load. It is also effective in mitigating influenza A (H1N1) infection and reducing the viral load on human nasal mucosal epithelia even when treatment is initiated only 24 hours post-infection.

Embodiments

1. An aqueous composition comprising a mucoadhesive polymer and clay particles.
2. The aqueous composition of embodiment 1, wherein the mucoadhesive polymer is selected from the group consisting of sodium alginate, chitosan, guar gum, xanthan gum, pectin, hydroxyethyl cellulose, hydroxypropyl cellulose, hydroxypropylmethyl cellulose, sodium carboxymethyl cellulose, poly(ethylene oxide), poly(acrylic acid), poloxamer (e.g. poloxamer 407), Avicel (e.g. Avicel RC591), and combinations thereof.
3. The aqueous composition of embodiment 2, wherein the mucoadhesive polymer is xanthan gum.
4. The aqueous composition of any one of embodiments 1-3, wherein the clay particles are selected from the group consisting of kaolin minerals such as kaolinite, china clay, dickite, nacrite, halloysite; serpentine minerals such as lizardite, halloysite, chrysotile, antigorite, carlosturanite, amestite, cronstedite, chamosite, berthierine, garierite; talc; pyrophyllite; ferripyrophyllite; smectites such as montmorillonites, beidellite, nontronite, hectorite, saponite, sauconite, medmontite, pimelite, bentonite; illite minerals such as ledikete, bravaisite, degraded mica, hydromica, hydromuscovite, hydrous illite, hydrous mica, K-mica, micaceous clay, and sericite; mica such as pegmatite, muscovite, and phlogopite; brittle mica such as margarite, and clintonite; glauconite; celadonite; chlorite and vermiculite such as pennine, clinochlore, chamosite, nimite, baileychlore, donbassite, cookite, sudoite, franklinfurnaceite; palygorskite and sepiolite minerals such as attapulgite; allophane and imogolite; mixed layer clay minerals such as talc-chlorite; and combinations thereof.
5. The aqueous composition of any one of embodiments 1-4, wherein the clay particles are bentonite.
6. The aqueous composition of any one of embodiments 1-5, comprising about 0.1% to about 3% by weight of the mucoadhesive polymer and about 0.4% to about 5% by weight of clay.
7. The aqueous composition of any one of embodiments 1-5, comprising about 0.1% to about 3% by weight of xanthan gum and about 0.4% to about 5% by weight of bentonite clay.
8. The aqueous composition of embodiment 7, comprising about 0.1% to about 0.5% by weight xanthan gum and about 2.0% to about 3.0% by weight of bentonite clay.
9. The aqueous composition of any one of embodiments 1-8, wherein the pH of the composition is from about 4 to about 7. For example, in any one of embodiments 1-8, the pH of the composition is about 5.
10. The aqueous composition of any one of embodiments 1-9, further comprising a buffer (e.g. citric acid).

11. The aqueous composition of any one of embodiments 1-10, wherein the composition includes one or more lipophilic excipients (e.g. caprylic/capric triglyceride).
12. The aqueous composition of embodiment 11, comprising about 0.1% to about 50% by weight of the lipophilic excipients.
13. The aqueous composition of embodiment 12, comprising about 30% to about 40% by weight of the lipophilic excipients.
14. The aqueous composition of any one of embodiments 1-13, further comprising a flavorant.
15. The aqueous composition of any one of embodiments 1-14, wherein the composition includes one or more moisturizing agents (e.g. glycerol).
16. The aqueous composition of embodiment 15, comprising about 0.1% to about 5% by weight of the moisturizing agents.
17. The aqueous composition of any one of embodiments 1-16, wherein the composition includes one or more viscosity modifiers (e.g. glyceryl stearate).
18. The aqueous composition of embodiment 17, comprising about 0.1% to about 50% by weight of the viscosity modifiers.
19. The aqueous composition of embodiment 17, comprising about 0.1% to about 5% by weight of the viscosity modifiers.
20. The aqueous composition of any one of embodiments 1-19, wherein the composition includes one or more preservatives and/or chelating agents (e.g. potassium sorbate, methyl paraben or disodium EDTA or potassium sorbate, methyl paraben, sodium benzoate, and/or disodium EDTA). In embodiments, the composition comprises one or more of: potassium sorbate, methyl paraben, sodium benzoate, phenoxyethanol, ethylhexylglycerin, pentylene glycol, hydroxyacetophonenone and/or disodium EDTA. For example, in embodiments the composition comprises, potassium sorbate. In embodiments the composition comprises, methyl paraben. In embodiments the composition comprises, sodium benzoate. In embodiments, the composition comprises, phenoxyethanol. In embodiments, the composition comprises ethylhexylglycerin. In embodiments, the composition comprises pentylene glycol. In embodiments, the composition comprises hydroxyacetophonenone. In embodiments the composition comprises, disodium EDTA.
21. The aqueous composition of embodiment 20, comprising about 0.01% to about 3% by weight of the preservatives and/or chelating agents.
22. The aqueous composition of embodiment 21, comprising about 0.1% to about 1.5% by weight of the preservatives and/or about 0.05% to about 0.5% by weight of the chelating agent.
23. The aqueous composition of any one of embodiments 1-22, wherein the composition has no more than 0.5% by weight of preservative (e.g. is free of preservatives).
24. The aqueous composition of any one of embodiments 1-23, wherein the composition comprises one or more antioxidants.
25. The aqueous composition of embodiment 24, comprising about 0.005% to about 0.5% by weight of the antioxidant.
26. The aqueous composition of embodiment 24 or 25, wherein the antioxidant is BHA.
27. The aqueous composition of any one of embodiments 1-26, wherein the composition is thixotropic.
28. The aqueous composition of any one of embodiments 1-27, wherein the composition exhibits non-Newtonian shear thinning viscosity.
29. The aqueous composition of any of embodiments 1-28, wherein the composition is an aqueous solution.
30. The aqueous composition of any of embodiments 1-28, wherein the composition is a gel emulsion (oil in water gel).
31. A method of treating or preventing infection in a subject, comprising administering a therapeutically effective amount of the aqueous composition of any one of embodiments 1-30 to the subject's mucosa, wherein the composition forms a barrier on the mucosa.
32. The method of embodiment 31, wherein the mucosa is a nasal, oral or pharyngeal mucosa.
33. The method of embodiment 31 or embodiment 32, wherein the infection is a respiratory viral infection.
34. The method of embodiment 33, wherein the respiratory viral infection is one or more of influenza, rhinovirus, coronavirus, and/or paramyxovirus infection.
35. The method of embodiment 34, wherein the coronavirus infection is selected from Severe Acute Respiratory Syndrome-Corona Virus (SARS-CoV), Middle East Respiratory Syndrome virus (CoV-MERS), human HCoV-229E, HCoV-OC43, HCoV-NL63 and HCoV-HKU1.
36. The method of embodiment 35, wherein the coronavirus infection is SARS-CoV-2.
37. The method of any one of embodiments 31-36, wherein the composition is administered as a spray or aerosol.
38. The method of embodiment 37, wherein the spray or aerosol is administered via a nasal pump spray or throat spray pump.
39. The method of any one of embodiments 31-36, wherein the composition is administered topically (e.g., as a cream, gel or ointment).
40. A method of preventing a COVID-19 infection in a subject, comprising administering a therapeutically effective amount of the aqueous composition of any one of embodiments 1-29, wherein the composition forms a barrier on the mucosa.
41. The method of embodiment 40, wherein the clay particles bind, trap, and/or inactivates SARS-CoV-2.
42. The method of any one of embodiments 31-41, wherein the composition comprises about 0.1% to about 3% by weight of xanthan gum and about 0.4% to about 5% by weight of bentonite clay.
43. A method for preventing or treating an allergic disease or condition in a subject in need thereof, comprising administering a therapeutically effective amount of the aqueous composition of any one of embodiments 1-30 to the subject's mucosa, wherein the composition forms a barrier on the mucosa.
44. The method of embodiment 43, wherein the allergic disease or condition is caused by or exacerbated by airborne allergens such as pollens, dust mites, molds, animal dander, and/or spores.
45. The method of embodiment 43 or 44, wherein the allergic disease is one or more of rhinitis, sinusitis, asthma, hypersensitive pneumonia, extrinsic allergic alveolitis, conjunctivitis, urticaria, eczema, dermatitis, anaphylaxis, angioedema, allergic and migraine headache.

The invention claimed is:

1. A sprayable aqueous intranasal composition comprising:
   about 0.1% to about 0.8% by weight of a mucoadhesive polymer;
   about 1.7% to about 2.8% by weight of a clay;
   about 30% to about 40% by weight of caprylic/capric triglyceride; and
   one or more chelating agents;
   wherein the composition has no more than 0.5% by weight of preservatives; and
   wherein the composition is thixotropic.

2. The sprayable aqueous intranasal composition of claim 1, wherein the clay is bentonite.

3. The sprayable aqueous intranasal composition of claim 1, wherein the mucoadhesive polymer is selected from the group consisting of sodium alginate, chitosan, guar gum, xanthan gum, pectin, hydroxyethyl cellulose, hydroxypropyl cellulose, hydroxypropylmethyl cellulose, sodium carboxymethyl cellulose, poly(ethylene oxide), poly(acrylic acid), poloxamer, blends of microcrystalline cellulose, sodium carboxymethyl cellulose, and combinations thereof.

4. The sprayable aqueous intranasal composition of claim 1, wherein the mucoadhesive polymer comprises xanthan gum.

5. The sprayable aqueous intranasal composition of claim 1, wherein the composition is free of preservatives.

6. The sprayable aqueous intranasal composition of claim 5, wherein the composition further comprises one or more antioxidants.

7. The sprayable aqueous intranasal composition of claim 1, wherein the one or more chelating agents are selected from the group consisting of ethylenediamine tetraacetic acid (EDTA), disodium EDTA, ethylenediamine-N,N'-disuccinic acid (EDDS), and combinations thereof.

8. The sprayable aqueous intranasal composition of claim 1, wherein the one or more chelating agents comprises disodium EDTA.

9. The sprayable aqueous intranasal composition of claim 1, wherein the pH of the composition is about 4 to about 7.

10. The sprayable aqueous intranasal composition of claim 9, wherein the pH of the composition is about 5 to about 6.8.

11. The sprayable aqueous intranasal composition of claim 1, further comprising about 3% to about 7% by weight of a moisturizing agent selected from the group consisting of glycerin, ethylene glycol, propylene glycol, propylene glycol 400, polyethylene glycol 400, hexalene glycol, butylene glycol, dextrose, glyceryl triacetate, polydextrose, glycerol, glyceryl triacetate, sorbitol, mannitol, and combinations thereof.

12. The sprayable aqueous intranasal composition of claim 1, wherein after spraying about 50 µL to about 200 µL of the composition to the nasal mucosa of a subject, the composition is retained on the nasal mucosa for about 20 minutes to about 5 hours.

13. The sprayable aqueous intranasal composition of claim 6, comprising:
   about 1.7% to about 2.8% by weight of bentonite;
   about 30% to about 40% by weight of caprylic/capric triglyceride;
   about 0.1% to about 0.8% by weight of xanthan gum;
   butylated hydroxyanisole, disodium EDTA;
   wherein the pH of the composition is about 4-7; and
   wherein after spraying about 50 µL to about 200 µL of the composition to the nasal mucosa of a subject, the composition is retained on the nasal mucosa for at least about 20 minutes to about 5 hours.

14. A nasal pump spray filled with the sprayable aqueous intranasal composition of claim 1.

15. The sprayable aqueous intranasal composition of claim 1, wherein the composition is an oil in water gel emulsion.

16. A method of reducing the infection of the nasal mucosa of a mammal by one or more harmful microorganisms comprising applying at least once per day an effective amount of the sprayable aqueous intranasal composition of claim 1 onto the nasal mucosa of the mammal.

17. A method of reducing the shedding of infectious viral pathogens from the nasal mucosa of a mammal infected with the pathogens comprising applying at least once per day an effective amount of the sprayable aqueous intranasal composition of claim 1 onto the nasal mucosa of the mammal.

18. A method of applying a barrier to the nasal mucosa of a mammal, comprising applying at least once per day an amount of the sprayable aqueous intranasal composition of claim 1 form a barrier layer on the nasal mucosa of the mammal.

19. The method of claim 16, wherein the effective amount of the sprayable aqueous intranasal composition ranges from about 50 µL to about 200 µL.

20. The method of claim 17, wherein the effective amount of the sprayable aqueous intranasal composition ranges from about 50 µL to about 200 µL.

21. The method of claim 18, wherein the amount of the sprayable aqueous intranasal composition ranges from about 50 µL to about 200 µL.

22. The method of claim 16, wherein the applying is by spraying three to eight times a day.

23. The method of claim 16, wherein the one or more harmful microorganisms comprise a virus from the Adenoviridae, Coronaviridae, Filoviridae, Flaviviridae, Hepadnaviridae, Herpesviridae, Orthomyxoviridae, Paramyxovirinae, Pneumovirinae, Picornaviridae, Poxyiridae, Retroviridae, or Togaviridae families.

24. The method of claim 23, wherein the virus is selected from the group consisting of a rhinovirus, coronavirus, parainfluenza virus, adenovirus, enterovirus, respiratory syncytial virus (RSV), bocavirus, influenza viruses, human metapneumovirus (hMPV), orthomyxoviridae, cytomegalovirus, Epstein-Barr virus, herpes simplex virus, and morbillivirus.

* * * * *